United States Patent [19]

McDonnell

[11] Patent Number: 5,506,102
[45] Date of Patent: Apr. 9, 1996

[54] METHODS OF USING THE A FORM OF THE PROGESTERONE RECEPTOR TO SCREEN FOR ANTAGONISTS OF STEROID INTRACELLULAR RECEPTOR-MEDIATED TRANSCRIPTION

[75] Inventor: Donald P. McDonnell, San Diego, Calif.

[73] Assignee: Ligand Pharmaceuticals Incorporated, San Diego, Calif.

[21] Appl. No.: 144,554

[22] Filed: Oct. 28, 1993

[51] Int. Cl.$^6$ .................................................. C12Q 1/68
[52] U.S. Cl. .............................. 435/6; 435/8; 435/69.1; 435/240.2; 435/810; 935/33; 935/34; 935/36
[58] Field of Search ................................ 435/6, 8, 240.2, 435/69.1, 810; 935/33, 34, 36

[56] References Cited

U.S. PATENT DOCUMENTS

| | | | |
|---|---|---|---|
| 4,981,784 | 1/1991 | Evans et al. | 435/6 |
| 5,071,773 | 12/1991 | Evans et al. | 436/501 |
| 5,262,300 | 11/1993 | Evans et al. | 435/6 |

OTHER PUBLICATIONS

Poletti et al., *Gene* 114, 51–58 (1992).
McDonnell et al., *J. Biol. Chem.* 269(16), 11945–11949 (1994).
McDonnell et al., *J. Steroid Biochem. Molec. Biol.* 48(5/6), 425–432 (1994).
Vegeto et al., *Molecular Endocrinology* 7(10), 1244–1255 (1993).
Kastner, P., et al., "Two Distinct Estrogen–Regulated Promoters Generate Transcripts Encoding the Two Functionally Different Human Progesterone Receptor Forms A and B," *The EMBO Journal,* (1990) vol. 9, No. 5, pp. 1603–1614.
Meyer, Marc–Etienne et al., "Agonistic and antagonistic activities of RU486 on the functions of the human progesterone receptor," *The EMBO Journal,* (1990) vol. 9, No. 12, pp. 3923–3932.
Lessey, Bruce A., et al., "The Subunit Structure of Human Breast Cancer Progesterone Receptors: Characterization by Chromatography and Photoaffinity Labeling," *Endocrinology,* (1983), vol. 112, No. 4, pp. 1267–1274.
Horwitz, Kathryn B., et al., "In Situ Photolinked Nuclear Progesterone Receptors of Human Breast Cancer Cells: Subunit Molecular Weights after Transformation and Translocation," *Endocrinology,* (1983) vol. 113, No. 6, pp. 2195–2201.
O'Malley, Bert, "The Steroid Receptor Superfamily: More Excitement Predicted for the Future," *Molecular Endocrinology,* (1990) vol. 4, No. 3, pp. 363–369.
Tora, Laszlo, et al., "The N–terminal region of the chicken progesterone receptor specifies target gene activation," *Nature,* (1988) vol. 333, pp. 185–188.

(List continued on next page.)

*Primary Examiner*—W. Gary Jones
*Assistant Examiner*—Kenneth R. Horlick

[57] ABSTRACT

Methods to screen for antagonists of steroid IR transcription as mediated by the PR-A isoform of the progesterone receptor are provided. Such cell-based methods include a cell in which PR-A is transcriptionally inactive containing asteroid IR other than PR, PR-A and a reporter vector that includes a promoter which is transcriptionally active in the presence of the steroid IR and an activator of said steroid IR, but is substantially transcriptionally inactive in the presence of PR-A. This cell is contacted with the activator of the steroid IR and a compound to be assayed, and the level of reporter product produced in the cell is measured and compared to the level of reporter product expressed in a similar cellular system absent PR-A as an indication of the potential antagonist activity of the compound being assayed. Also provided are an assay kit, a method of screening PR active compounds as ER antagonists and compounds that inhibit the transcriptional activity of asteroid IR in the presence of PR-A in a cellular context where PR-A is substantially transcriptionally inactive.

19 Claims, 14 Drawing Sheets

Adapter Limiting

OTHER PUBLICATIONS

Takimoto, Glenn S., et al., "Hormone–induced progesterone receptor phosphorylation consists of sequential DNA–independent and DNA–dependent stages: Analysis with zinc finger mutants and the progesterone antagonist ZK98299," *Proc. Natl. Acad. Sci. USA,* (1992) vol. 89, pp. 3050–3054.

Klein–Hitpass, Ludger, et al., "Two types of antiprogestins identified by their differential action in transcriptionally active extracts from T47D cells," *Nucleic Acids Research,* (1991) vol. 19, No. 6, pp. 1227–1234.

Clarke, C. L., et al., "Progestin Regulation of Cellular Proliferation," 11 *Endocrine Rev.,* 266–301 (1990).

Conneely, O. M., et al., "The A and B Forms of the Chicken Progesterone Receptor Arise by Alternate Initiation of Translation of a Unique mRNA," *Biochem. Bioph. Res. Comm.,* 493–501 (1987).

Christensen, K., et al., "Characterization and Functional Properties of the A and B forms of Human Progesterone Receptors Synthesized in a Baculovirus System," 5 *Mol. Endocrinol.* 1755–1770 (1991).

Klein–Hitpass, L., et al., "The Progesterone Receptor Stimulates Cell–free Transcription by Enhancing the Formation of a Stable Pre–initiation Complex," 60 *Cell,* 247–257 (1990).

Bocquel, M. T., et al., "The Contribution of the N— and C—terminal regions of steroid receptors to activation of transcription is both receptor and cell–specific," *Nucleic Acids Research,* (1989) vol. 17, No. 7, pp. 2581–2595.

Evans, Ronald M., "The Steroid and Thyroid Hormone Receptor Superfamily," *Science,* (1989) vol. 240, pp. 889–895.

Beato, Miguel, "Gene Regulation by Steroid Hormones," *Cell,* (1989) vol. 56, pp. 335–344.

Schrader, William T., et al., "Progesterone–binding Components of Chick Oviduct," *The Journal of Biological Chemistry,* (1972) vol. 247, No. 1, pp. 51–59.

Meyer, Marc–Etienne, et al., "A Limiting Factor Mediates the Differential Activation of Promoters by the Human Progesterone Receptor Isoforms," *The Journal of Biological Chemistry,* (1992) vol. 267, No. 15, pp. 10882–10887.

Berger, Tina S., et al., "Interaction of Glucocorticoid Analogues with the Human Glucocorticoid Receptor," *J. Steroid Biochem. Molec. Biol.* (1992) vol. 41, No. 3–8, pp. 733–738.

Shemshedini, Lirim, et al., "In Vitro Activity of the Transcription Activation Functions of the Progesterone Receptor, Evidence for Intermediary Factors," *The Journal of Biological Chemistry,* (1992) vol. 267, No. 3, pp. 1834–1839.

Vegeto, Elisabetta, et al., "The Mechanism of RU486 Antagonism is Dependent on the Conformation of the Carboxy–Terminal Tail of the Human Progesterone Receptor," *Cell,* (1992) vol. 69, pp. 703–713.

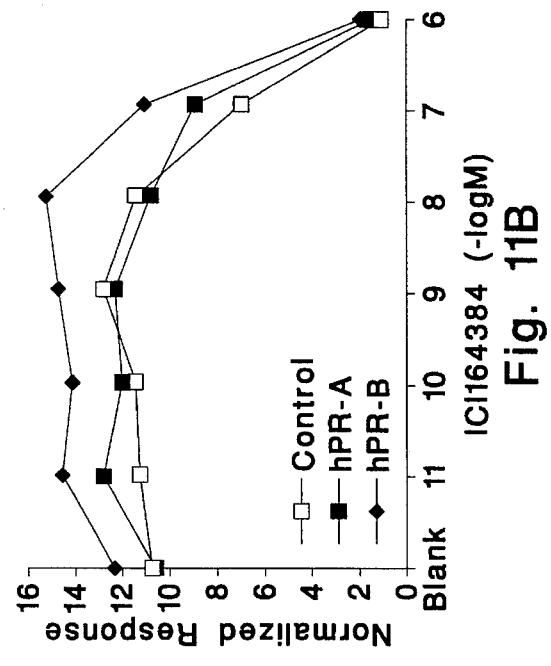
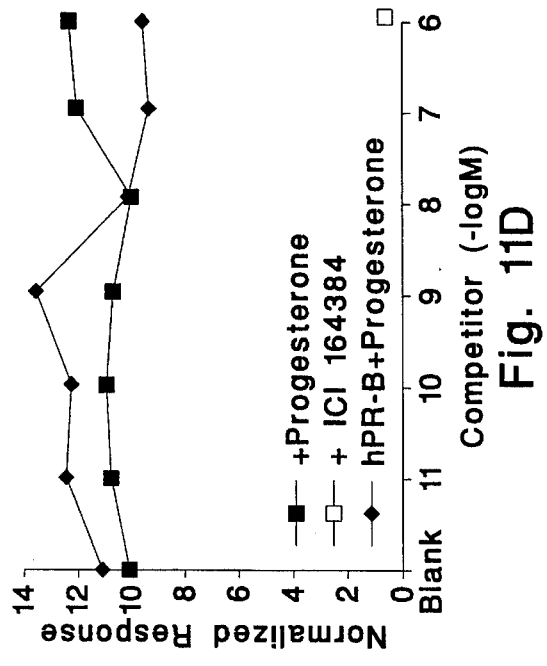
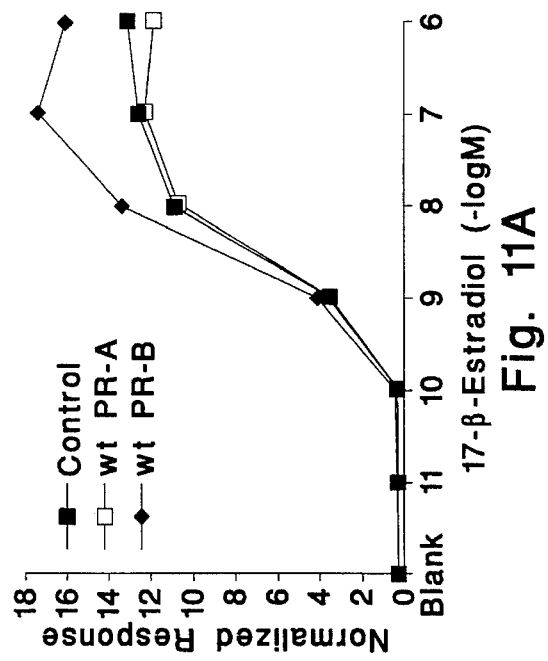
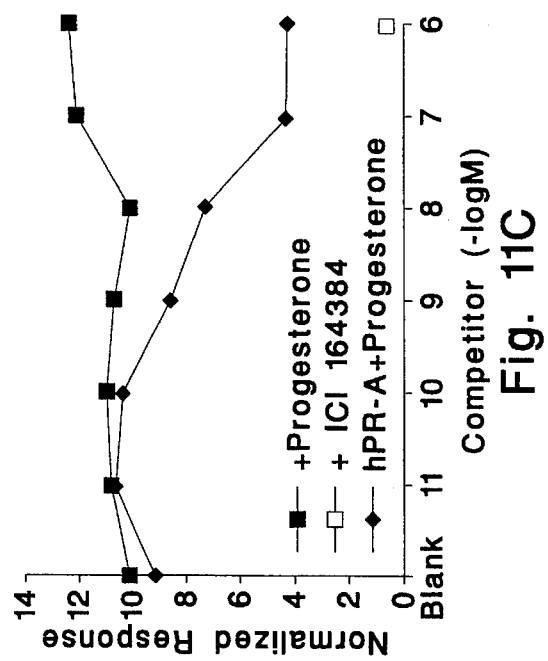

METHODS OF USING THE A FORM OF THE PROGESTERONE RECEPTOR TO SCREEN FOR ANTAGONISTS OF STEROID INTRACELLULAR RECEPTOR-MEDIATED TRANSCRIPTION

FIELD OF THE INVENTION

This invention relates to methods and assays useful to screen for compounds that regulate the transcriptional activity of intracellular receptors and to compounds that mediate transcription.

BACKGROUND OF THE INVENTION

The steroid hormone progesterone is a potent hormonal effector implicated in the control of proliferation, differentiation and development of mammary and uterine tissues. Clark, C. L. and R. L. Sutherland, Progestin Regulation of Cellular Proliferation, 11 *Endocrine Rev.*, 266–301 (1990). The endocrine effects of this hormone are manifest only in cells containing a specific intracellular receptor, the progesterone receptor (PR). The interaction between PR and its cognate ligand (progesterone) induces a series of structural and functional changes in the protein, leading ultimately to an association of the receptor with specific DNA sequences in the regulatory regions of target genes. The cellular and promoter context of the bound receptor determines the phenotypic consequence of this interaction. O'Malley, B. W., The Steroid Receptor Superfamily: More Excitement Predicted for the Future, 4 *Mol. Endocrinol.*, 363–369 (1990); Beato, M., Gene Regulation by Steroid Hormones, 56 *Cell* 335–344 (1989).

The progesterone receptor (PR) is a member of a closely related sub-group of intracellular receptors that includes the androgen, mineralocorticoid, glucocorticoid and estrogen receptors. Evans, R. M., The Steroid and Thyroid Receptor Superfamily, 240 *Science*, 889–895 (1988). Within this sub-group, human PR is unique in that it occurs in target tissues as two distinct subtypes, PR-A and PR-B, of 94 and 114 kDa, respectively. Schrader, W. T. and B. W. O'Malley, Progesterone-Binding Components of Chick Oviduct: Characterization of Purified Subunits, 247 *J. Biol. Chem.*, 51–59 (1972); Horwitz, K. B. and P. S. Alexander, In situ Photo-linked Nuclear Progesterone Receptors of Human Breast Cancer Cells: Subunit Molecular Weights After Transformation and Translocation, 113 *Endocrinology*, 2195–2201 (1983). The PR-B isoform contains an N-terminal fragment of 164 amine acids (B 164) which is absent on the PR-A isoform. It is likely that both forms can arise as a result of either alternate initiation of translation from the same mRNA or by transcription from alternate promoters within the same gene. Conneely, O. M., Maxwell, B. L., Toft, D. O., Schrader, W. T. and B. W. O'Malley, The A and B Forms of the Chicken Progesterone Receptor Arise by Alternate Initiation of Translation of a Unique mRNA, 149 *Biochem. Bioph. Res. Comm.*, 493–501 (1987); Kastner, P., Krust, A., Turcotte, B., Stropp, U., Tora, L., Gronemeyer, H. and P. Chambon, Two Distinct Estrogen-Regulated Promoters Generate Transcripts Encoding the Two Functionally Different Human Progesterone Receptor Forms A and B, 9 *EMBO J.*, 1603–1614 (1990). Interestingly, Kastner et al., have identified two distinct promoters in the hPR gene. These promoters which regulate the synthesis of specific transcripts corresponding to hPR-A and hPR-B are regulated independently. Id. It is likely therefore, that the expression levels of PR-A and PR-B can differ with respect to each other in certain target tissues.

The biochemical properties of the PR isoforms have been analyzed in vitro, where they displayed similar DNA and hormone binding affinities. Lessey, B. A., Alexander, P. S. and K. B. Horwitz, The Subunit Structure of Human Breast Cancer Progesterone Receptors: Characterization by Chromatography and Photoaffinity Labeling, 112 *Endocrinology*, 1267–1283 (1983); Christensen, K., Estes, P. A., Onate, S. A., Beck, C. A., DeMarzo, A., Altmann, M., Lieberman, B. A., St. John, J., Nordeen, S. K. and D. P. Edwards, Characterization and Functional Properties of the A and B Forms of Human Progesterone Receptors Synthesized in a baculovirus System, 5 *Mol. Endocrinol.*, 1755–1770 (1991). However, when analyzed in reconstituted progesterone response systems in heterologous cells it became apparent that hPR-A and hPR-B have different promoter specificities. Kastner et al.; Meyer, M. E., Pornon, A., Ji, J., Bocquel, M. T., Chambon, P. and H. Gronemeyer, Agonist and Antagonist Activities of RU486 on the Functions of the Human Progesterone Receptor, 9 *EMBO J.*, 3923–3932 (1990). A similar result was obtained when the transcriptional activities of chicken PR-A and PR-B were assessed. Tora, L., Gronemeyer, H., Turcotte, B., Gaub, M. P. and P. Chambon, The N-terminal Region of the Chicken Progesterone Receptor Specifies Target Gene Activation, 333 *Nature*, 185–188 (1988); Bocquel, M. T., Kumar, V., Stricker, C., Chambon, P. and H. Gronemeyer, The Contribution of the N- and C-terminal Regions of Steroid Receptors to Activation of Transcription is both, Receptor and Cell-specific, 17 *Nucleic Acids Res.*, 2581–2595 (1989).

Two distinct regions within hPR required for transcriptional activation (TAFs) have been identified, TAF1 located in the amino terminus and TAF2 within the carboxyl terminus. Interestingly, both TAFs are contained within PR-A and PR-B. The B164 region, unique to hPR-B, does not contain additional transcriptional activators but is required for maximal TAF1 function in the context of the full-length receptor. Meyer, M. E., Qurin-Stricker, C., Lerouge, T., Bocquel, M. T. and H. Gronemeyer, A Limiting Factor Mediates the Differential Activation of Promoters by the Human Progesterone Receptor Isoforms, 267 *J. Biol. Chem.*, 10882–10887 (1992). It is possible, therefore, that in cell and promoter contexts where TAF1 activity is required, that PR-B will be a more efficient transcriptional regulator than PR-A.

The precise mechanism by which the promoter bound receptor exerts its transcriptional effect is unclear at present. The reconstitution of steroid receptor dependent transcription in vitro has been informative in this regard. Klein-Hitpass, L., Tsai, S. Y., Weigel, N. L., Allan, G. A., Riley, D., Rodriguez, R., Schrader, W. T., Tsai, M. J. and B. W. O'Malley, The Progesterone Receptor Stimulates Cell-free Transcription by Enhancing the Formation of a Stable Pre-initiation Colnflex, 60 *Cell*, 247–257 (1990). On chromatin free templates it is clear that at least one of the functions of the receptor is to recruit and/or stabilize the transcription pre-initiation complex at the core promoter. It is probable, however, that in the context of the intact cell, additional factors and processes in unison with the activated receptor are required for appropriate function. The existence of "adapters" or "co-factors" which influence the interaction between bound receptor and the general transcription apparatus has been implicated by several studies. Shemshedin, L., Ji, J., Brou, C., Chambon, P. and H. Gronemeyer, In vitro Activity of the Transcription Activation Functions of the Progesterone Receptor, 267 *J. Biol. Chem.*, 1834–1839 (1992); Tora et al. It is likely that these "co-factors" are differentially expressed in cells and in the case of the progesterone receptor may be the determinants of the cellular and promoter context preferences of the PR-A and PR-B.

General assays and methods for detecting the transcriptional activity of an intracellular receptor (IR) when exposed to a known ligand or unknown compound have been developed. For example, U.S. Pat. No. 5,071,773, describes an assay by which hormone IRs, ligands for these receptors, and proteins having transcriptional activating properties of a hormone IR can be identified. Generally, the assay involves use of a cell which contains both DNA encoding a hormone response element (i.e., a promoter) linked to an operative reporter gene and DNA encoding an IR protein. When a suitable hormone or ligand is exposed to the cell, a hormone-IR complex forms and is delivered to an appropriate DNA binding region, thereby activating the hormone response element, which in turn leads to expression of the product encoded by the reporter gene. Thereafter, activation of the reporter gene is detected by standard procedures used for detecting the product of a reporter gene, as an indication of the relative transcriptional activity of the hormone or ligand on the cellular system.

SUMMARY OF THE INVENTION

The present invention provides methods and assays useful to screen compounds that are potential antagonists of steroid intracellular receptor (IR) mediated transcription other than progesterone receptor, as well as agonists and antagonists of PR mediated transcription. These methods and assays are based on the surprising discovery that, in a given cellular and promoter context, the PR-A isoform of the human progesterone receptor (PR) is inactive, and acts as potent transdominant repressor of PR-B mediated transcription. Even more surprising, in a given cellular and promoter context, PR-A functions as a receptor specific repressor of transcription of the glucocorticoid receptor (GR), androgen receptor (AR), mineralocorticoid receptor (MR) and estrogen receptor (ER).

In particular, the present invention provides a method for screening for antagonism of steroid IR mediated transcription comprising (a) introducing a first vector encoding asteroid IR other than PR and a second vector encoding PR-A along with a third reporter vector into a cell in which PR-A is substantially transcriptionally inactive, wherein the reporter vector includes a gene encoding a reporter product and a promoter which is transcriptionally active in the presence of the steroid IR and an activator of said steroid IR, but is substantially transcriptionally inactive in the presence of PR-A, (b) contacting the cell with the activator of steroid IR transcription and a second compound, and (c) comparing the level of reporter product expressed in the cell relative to the level of reporter product expressed in a second cell containing the steroid IR and reporter vector, and contacted with the activator and second compound, as an indication of the potential antagonist activity of the second compound on steroid IR transcription. In addition, this method can further comprise contacting a third cell containing a PR isoform and a reporter construct with an activator of PR transcription and the second compound, wherein the PR isoform is transcriptionally active in the third cell, and comparing the level of reporter product expressed in the third cell relative to the level of reporter product expressed in the third cell in the absence of the second compound.

The present invention also provides an assay kit to screen for antagonists of steroid IR transcription comprising a first cell containing asteroid IR other than PR, PR-A, a reporter vector including a gene encoding a reporter product and a promoter which is transcriptionally active in the presence of the steroid IR and an activator of said steroid IR, but is substantially transcriptionally inactive in the presence of PR-A, a second cell containing the steroid IR and reporter vector, and the activator of steroid IR transcription, wherein PR-A is substantially transcriptionally inactive in the first cell, and wherein the contacting of the first cell with the activator and a compound to be assayed yields a level of expressed reporter product that can be compared to the level of expressed reporter product in the second cell when contacted with the activator and second compound, as an indication of the potential antagonist activity of the compound to be assayed on steroid IR transcription.

The present invention further provides a method for screening PR active compounds for ER antagonist activity comprising (a) introducing a first vector encoding ER and a second vector encoding PR-A along with a third reporter vector into a cell in which PR-A is substantially transcriptionally inactive, wherein the reporter vector includes a gene encoding a reporter product and a promoter which is transcriptionally active in the presence ER and an ER agonist, but is substantially transcriptionally inactive in the presence of PR-A, (b) contacting the cell with the ER agonist and a PR active compound, and (c) comparing the level of reporter product expressed in the cell relative to the level of reporter product expressed in a second cell containing ER and the reporter construct, and contacted with the ER agonist and PR active compound, as an indication of the potential antagonist activity of the PR active compound on ER transcription.

The present invention further yet provides compounds that inhibit the transcriptional activity of asteroid IR in the presence of PR-A, and in a cellular context in which PR-A is substantially transcriptionally inactive.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWINGS

The invention may be further illustrated by reference to the accompanying Drawings wherein:

(FIG. 10A) The cells were treated with no hormone (NO H), $10^{-7}$M progesterone (PROG), $5 \times 10^{-8}$M dihydrotestosterone (DHT), $10^{-7}$M ZK112993 (ZK993) or $10^{-7}$M ZK98299 (ZK299) for 24 hours. The relative luciferase activity is calculated by dividing the normalized luciferase value at a given point by that obtained in the absence of transfected receptor or ligand. (FIG. 10B) Cells were grown in the presence of $10^{-8}$M DHT alone or in the presence of $10^{-7}$M progesterone, antiprogestin ZK112993 or antiprogestin ZK98299 as indicated. The data are presented as percent (%) activation, where 100% represents the maximal induction achieved by human androgen receptor at $10^{-8}$M DHT. The experimental data represents mean values +/− the average deviation from the mean of quadruplicate estimations;

FIGS. 11A–11D are a series of graphs showing CV-1 cells that were transiently transfected with vectors expressing either the human estrogen receptor (pRST7hER) alone (Control), or in combination with vectors expressing either the human progesterone receptor isoform PR-A (pSVhPR-A) or PR-B (pSVhPR-B), along with reporter plasmid MMTV-ERE-LUC, as indicated. The transcriptional activity in these cell cultures was measured following the addition of (FIG. 11A) increasing concentrations of 17-β-estradiol (FIG. 11B) increasing concentrations of the pure anti-estrogen ICI-164,384 in the presence of a saturating concentration of 17-β-estradiol ($10^{-7}$M), and in (FIG. 11C) and (FIG. 11D) with increasing concentrations of progesterone in the presence of $10^{-7}$M 17β-estradiol. All values were normalized for transfection efficiency by simultaneous estimation of luciferase and β-galactocidase activities. The relative luciferase activity is calculated by dividing the normalized luciferase value at a given point by that obtained in the absence of transfected receptor or ligand. Data shown represent the mean +/− the average deviation from the mean of triplicate estimations. The average co-efficient of variation at each hormone concentration was less than 15%;

DETAILED DESCRIPTION OF EMBODIMENTS OF THE INVENTION

Figure 1A:
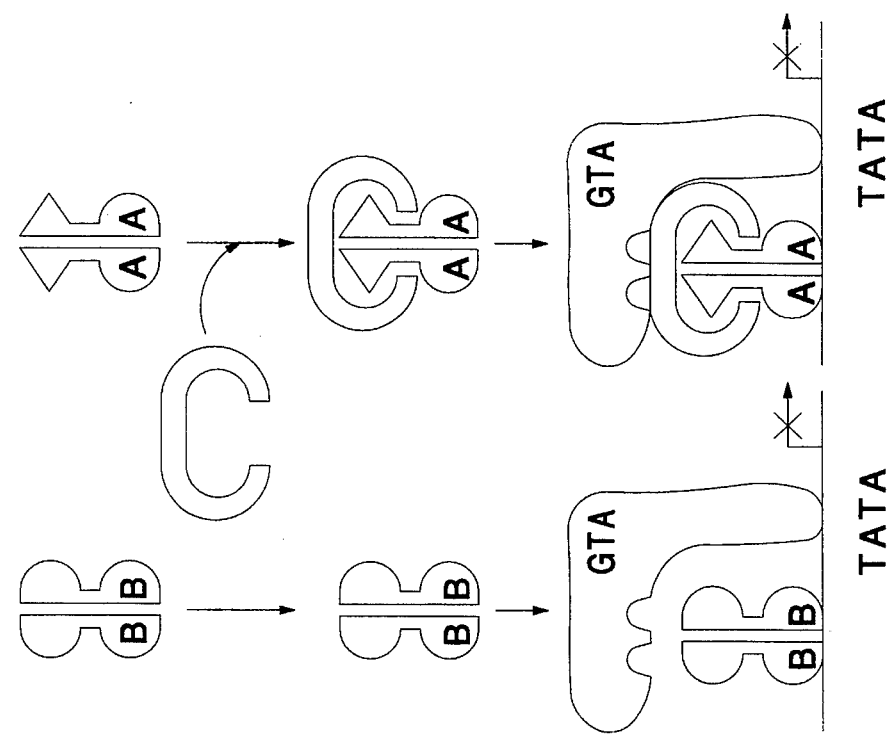
FIGS. 1A–1B are a schematic illustration of a proposed model of the mechanism by which PR-A functions as a transdominant repressor of PR-B function in given cellular and promoter contexts.

In a first aspect, the present invention provides a method for screening for antagonists of steroid intracellular receptor (IR) mediated transcription. In this method, a cell in which the PR-A isoform of the human progesterone receptor (PR) is transcriptionally inactive is transiently transfected with a vector containing the cDNA for asteroid IR other than PR (i.e., AR, MR, GR or ER), a vector containing the cDNA for the PR-A isoform of human PR and a reporter vector which includes a gene encoding a reporter product, such as the luciferase gene, joined to a promoter that is transcriptionally active in the presence of the steroid IR, but substantially transcriptionally inactive in the presence of PR-A. See e.g., U.S. Pat. No. 5,071,773, the disclosure of which is herein incorporated by reference. In this regard, the monkey kidney fibroblast CV-1 cell line in combination with a reporter vector including the luciferase gene joined to the mouse mammary tumor virus (MMTV) promoter provides a suitable environment where the human PR-A isoform is transcriptionally inactive.

After establishing the vectors in the appropriate cellular context, and allowing a sufficient period of time for expression of the PR-A and steroid IR proteins within the cell, the cell is contacted and incubated with a known activator of transcription for the steroid IR (e.g., dexamethasone with GR), and a second compound that is being screened for its potential antagonist activity on ligand mediated transcription from the steroid IR. Thereafter, the level of reporter product (e.g. luciferase) expressed within the cell is recorded and compared to the level of the same reporter product expressed in an analogous cell-based system contacted with the activator and second compound, but lacking the PR-A vector and expression product, as an indication of the antagonist action of the second compound on the steroid IR mediated transcription.

The above-described method will prove useful in the detection of compounds which display antagonist activity in vivo. In this regard, the present method assumes that cellular contexts in which PR-A is inactive and coexpressed with another steroid IR, such as GR, AR, MR or ER, will occur in the animal or human subject to be treated. With the identification of such tissues, steroid IR antagonists can be discovered and designed that have tissue specific activity within the patient to be treated. This in turn will prove useful in the treatment of various hormone activated, tissue-specific cancers and other maladies, including breast cancer and ovarian cancer. Evidence of such cellular contexts in vivo have been observed, but unexplained till present. For example, in primate uterus, the antiprogestin RU-486 also inhibits estrogen stimulated uterine proliferation. Slayden, O. D., Hirst, J. J. and R. M. Brenner, 132 *Endocrinology*, 1845–1856 (1993); Slayden, O. D. and R. M. Brenner, *Endocrinology*, (In press, 1993). However, in the oviducts of the same animal, RU-486 only manifests anti-progestenic activity. Id. In this regard, it has also been shown that PR-A is well expressed in the endometrium throughout the human menstrual cycle, suggesting that the contraceptive efficacy of RU-486 may relate to both its potential to function as an anti-progestin in late cycle and as an anti-estrogen throughout the cycle.

Once an effective antagonist of asteroid IR other than PR is identified according to the above-described method, further screening of the compound can be undertaken to determine the PR activity of the compound. In particular, further screening will determine whether the compound is an agonist or antagonist of PR in cellular contexts other than that of the above method (i.e., in cellular contexts where PR-A and PR-B are transcriptionally active versus contexts where PR-A is transcriptionally inactive). This determination of PR activity can be accomplished via one or more follow-on assays.

In one aspect, the steroid antagonist compound is contacted with a third cell containing an isoform of PR (i.e. either or both PR-A and PR-B) and a reporter vector. Importantly, both the cell type (e.g., a HepG2 cell) and promoter (e.g., the MMTV promoter) of the reporter vector are transcriptionally active in the presence of the expressed PR isoform. After an appropriate period of incubation with the selected compound, the level of reporter product expressed in the cell is compared with the level of the same reporter product expressed in the same cell, but absent the expressed PR isoform. If the level of reporter product expressed in the cell containing the PR isoform is higher than that in the cell without the PR isoform, then the tested compound is a PR agonist in cellular contexts where PR is transcriptionally active.

If the level of expressed reporter product in the above system is substantially identical, then the compound can be tested for PR antagonist activity in the same cellular system, except the compound being tested is concurrently incubated with a known activator of PR transcription. The degree to which the reporter product expressed in the cell incubated with both the PR activator and compound being tested is depressed relative to the level of reporter product expressed in the same cell incubated only with the PR activator provides a relative measure of the antagonist activity of the tested compound on PR mediate transcription. In this regard, the above-described assays for PR agonist and antagonist activity can be run in either order with the compound to be tested. Thus, in another aspect, the steroid IR antagonist discovered by the method of the present invention can first be tested for PR antagonist activity relative to a known PR activator, and if need be, subsequently tested for PR agonist activity as described above.

In a second aspect, the present invention also provides methods to screen known PR active compounds (i.e. PR agonists and antagonists) for ER antagonist activity in a given cellular and promoter context. In such an assay, a vector encoding ER and a vector encoding PR-A, as well as a reporter vector are introduced into a cell in which PR-A is substantially transcriptionally inactive, and in which the promoter of the reporter vector is transcriptionally active in the presence of ER, but substantially transcriptionally inactive in the presence of PR-A. The cell is then contacted with an ER agonist and a known PR active compound, and the level of reporter product expressed in such a system is compared the level of the same reporter product expressed in the same cellular system absent the PR-A as an indication of the antagonist action of the PR active compound on ER mediated transcription.

In yet a further aspect, the present invention provides compounds other than RU486, aka mifepristone (11β-(4-dimethylaminophenyl)-17β-hydroxy-17α-(1-propynyl)-4,9-estradien-3-one) that inhibit the transcriptional activity of asteroid IR in the presence of PR-A, and in a cellular context in which PR-A is substantially transcriptionally inactive. Thus, compounds that are PR active (e.g. agonists and/or antagonists), and which in the proper cellular context in combination with PR-A, inhibit transcription from the steroid IRs, including MR, AR, GR, ER and PR-B, are considered to be within the scope of the present invention.

It is to be understood that the methods of the present invention are not limited to the transfection, or other means of introduction of the steroid IR and PR-A vectors, and thereby the expressed proteins, into a given cell. Thus, while it is preferred to employ a cell line substantially void of endogenous PR, AR, MR, GR or ER, such as CV- 1 cells, it is also possible to employ a cell line in which one or more of the receptors of choice are endogenous to the cell, as long as any expressed PR-A is substantially transcriptionally inactive in that cell line.

Using the methods of the present invention, assay kits can be constructed and used to discover steroid antagonist ligands and PR agonist and antagonist ligands in a drug discovery effort. For example, an assay kit with a first cell in which PR-A is transcriptionally inactive containing asteroid IR other than PR, PR-A and a reporter vector, including a promoter with is active in the presence of the steroid IR but substantially transcriptionally inactive in the presence of PR-A, a second cell containing the steroid IR and reporter vector, and a known activator of steroid IR transcription can be provided and used with the above described methods to test compounds for their antagonist activity on steroid IR mediated transcription.

The methods of the present invention are based upon the surprising observation that, in given promoter and cellular contexts where the PR-A isoform of the human progesterone receptor (PR) is transcriptionally inactive, it functioned as an extremely potent, ligand-dependent repressor of the transcriptional activity of the PR-B isoform of human PR. Further, this PR-A inhibition effect was dominant, since repression was detected even at substoichiometric concentrations of PR-A. Even more surprisingly, PR-A also functions as a repressor of MR, AR, GR and ER mediated transcription in such inactive cellular and promoter contexts. However, in other cellular and promoter contexts were PR-A is active, it functions as a transcriptional activator, for example, as shown by its activity in HeLa cells where PR-A effectively stimulated the tyrosine amino transitrase (TAT) promoter in a hormone-dependent manner.

The PR-A receptor exhibits its dominant repressive effect on all members of the steroid family of intracellular receptors in a promoter and cell specific manner. However, to date PR-A has not shown any effects on a vitamin D receptor mediated regulation of a VDRE-tk promoter. Likewise, the transcriptional activity of the SV40 or Rous Sarcoma Virus promoters were unaffected by PR-A expression.

The methods of the present invention, and the compounds having specific activity discovered with those methods, do not require binding of the PR-A isoform to DNA for PR-A repression of transcription to occur. In fact, two lines of investigation demonstrated that repression by PR-A occurred independently of DNA binding. First a mutant of PR-A (PR-A587); bearing a point mutation in the DNA binding domain, functioned as an efficient repressor of PR-B mediated transactivation. Second, the anti-progestin ZK98299, which binds to PR and retards DNA binding, promotes PR-A repressor function.

The promoter and cell specificity coupled with the stoichiometry indicate that the mechanism for PR-A-mediated repression differs from the more general "squelching" or transcriptional interference event that occurs as a result of over-expression of some transcription factors. In this regard, ligand-dependent, DNA binding-independent, cross interference between the estrogen receptor (ER) and PR or GR has been reported previously. Adler, S., Waterman, M. L., He, X. and M. G. Rosenfeld, Steroid Receptor-mediated Inhibition of Rat Prolactin Gene Expression does not Require the Receptor DNA-binding Domain, 52 *Cell*, 685–695 (1988). In addition, ER over-expression effectively down-regulates prolactin gene expression, a process occurring also independently of DNA binding. Adler, A. J., Danielsen, M. and D. M. Robins, Androgen-specific Gene Activation via a Consensus Glucocorticoid Response Element is Determined by Interaction with Nonreceptor Factors, 89 *Proc. Natl. Acad. Sci.*, 11660–11663 (1992). However, in contrast with the mechanism encountered for PR-A repression, antagonists of the interfering receptor do not promote "squelching". Significantly, the transdominant effects of PR-A on AR, MR, PR-B and GR are induced by all agonists and antagonists of the progesterone receptor.

Figure 1B:
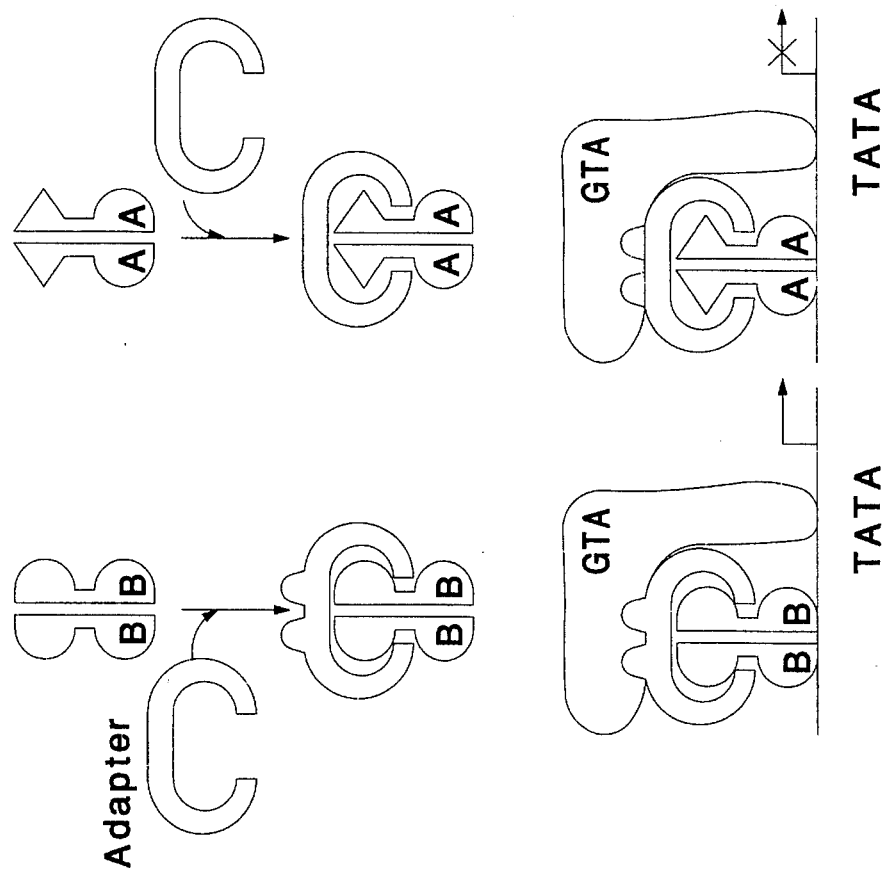

While not being held to a theory of operation, we propose that on promoters where PR-B (or a member of the steroid IR family) is transcriptionally active and PR-A is not, PR-A binds with greater affinity but in a non-productive manner to a co-factor required for PR-B function. As illustrated in FIG. 1A, when this adapter or cofactor is in abundant supply within the cell, the PR-B isoform can dimerize, bind to the adapter and interact with the General Transcription Apparatus (GTA) to promote transcription of the gene product. This occurs even though the PR-A isoform displays a higher affinity for the adapter than does the PR-B isoform. However, in a cellular context where the adapter is limiting, as illustrated in FIG. 1B, then the high affinity of PR-A for the adapter will remove all or essentially all of the adapter from the system. In such an instance, PR-B, or the other steroid IRs (e.g., AR, MR, GR and ER) would be denied access to the adapter, and accordingly could not bring about transcription of the gene product via the GTA. Thus, the requirement for this interaction ultimately would be determined by cell context, such that the same promoter could be differentially activated, depending on the cellular complement of transcription factors. On other promoters where both A and B are active, there may be no requirement for such additional co-factors, or a different class of transcriptional factors utilized by both isoforms are recruited, or the quantities of common co-factors are in vast excess.

The invention will be further illustrated by reference to the following non-limiting Examples.

EXPERIMENTAL PROCEDURES

Chemicals

Restriction and modification enzymes were obtained from Promega Biotec (Madison, Wis.), Boehringer Mannheim (Indianapolis, Ind.), or New England Biolabs (Bethesda, Md.). PCR reagents were obtained from Perkin Elmer Cetus (Norwalk, Conn.). [1,2-$^3$H] progesterone (47.3 Ci/mmol) was purchased from Amersham (Arlington Heights, Ill.). Chemicals were purchased from Sigma Chemical (St. Louis, Mo.). Secondary and alkaline phosphatase-conjugated antibodies for Western analysis were obtained from BioRad (Richmond, Calif.). Immobilon-P (PVDF) transfer membranes were purchased from Millipore (Bedford, Mass.).

Construction of the Receptor Expression Vectors

The plasmid phPR-B (available from Dr. Geoff Greene, Ben May Institute, Chicago, Ill.), containing the cDNA for the PR-B isoform of the human progesterone receptor under the control of the SV40 enhancer/human metallothionein-II promoter, was digested with BamHI restriction enzyme. See e.g., Vegeto, et al., 69 *Cell* 703 (1993), the disclosure of which is herein incorporated by reference. Of the three resulting DNA fragments (5.1, 2.7 and 0.24 Kb) only two (5.1 and 2.7 Kb) were isolated. The ligation of the correctly-oriented fragments resulted in a plasmid, called phPR-A, which was identical to phPR-B except it lacked the 245 bases that contain the ATG sequence for the B isoform. For the construction of the DNA binding mutant of hPR-A (i.e. hPR-A587), we followed the procedure described by Takimoto et al., 89 *P.N.A.S.* 3050 (1992). Specifically, cystine No. 587 was substituted with an alanine by PCR using primers carrying a double-point mutation (5'-3'-CCT-GTGGGAGCGCTAAGGTCTTC (SEQ. ID. No. 1) and its 3'-5'-oriented counterpart) synthesized by National Biosciences Inc. (Plymouth, Minn.). The presence of the double point mutation in the receptor molecule was verified by DNA sequencing.

The construction of the plasmids pRShGR, pRShMR, and pRShVDR have been described previously by Arriza et al., 237 *Science* 268 (1989); Giguere et al., 46 *Cell* 645 (1986); Umesono et al., 65 *Cell* 1255 (1991), the disclosures of which are herein incorporated by reference. These expression vectors utilize the Rous Sarcoma Virus promoter and SV40 polyadenylation signal.

The plasmids pRST7hPR-A and pRST7hPR-B were constructed as follows. The plasmids YepPR-B and YepPR-A891, containing the full length hPR-B and a truncated hPR-A were cleaved with BamHI. Vegeto et al., 69 *Cell*, 703–713 (1992). This release the PR-A and PR-A891 DNA's respectively. These fragments were cloned into the cognate site of the pRST7 expression vector (P. Syka, Ligand Pharmaceuticals, Inc., San Diego, Calif.), giving rise to pRST7hPR-A and pRST7hPR-A891 respectively.

The construct pRST7hPR-B891 was derived as follows. YephPR-B891 was digested with AflII and KpnI. The 3 Kb fragment arising from this digestion was purified and modified with T4 DNA polymerase and digested with BamHI. The resulting fragments (0.2 Kb and 2.8 Kb) were cloned into an EcoRV/BamHI prepared pRST7 vector. The plasmid pRST7hPR-B was constructed by replacing the BstEII/KpnI fragment of pRST7hPR-B891 with the analogous fragment from pRST7hPR-A. All constructions were sequenced for validation.

The plasmid pRShAR was created as follows. The human androgen receptor cDNA was obtained from Androbio Inc. Chicago. It was excised from the carrier plasmid (pGEM3Z) by BglII and BamHI digestion. The DNA fragment corresponding to the AR cDNA was purified and then cloned into the BamHI site of the pRS mammalian expression vector.

Construction of the Reporter Plasmids

For the construction of PRE$_2$tk-LUC, the MMTV-LTR promoter sequence of MMTV-LUC reporter plasmid disclosed in Berger et al., 41 *J. Steroid Biochem. Mol. Biol.* 733 (1992), the disclosure of which is herein incorporated by reference, was substituted with the PRE$_2$tk sequence from PRE$_2$tk-CAT plasmid (available from Dr. Bert O'Malley, Baylor College of Medicine, Houston, Tex.) (PRE$_2$tk-CAT contains two copies of the human progesterone responsive element (PRE) of the tyrosine aminotransferase (TAT) promoter linked to the Herpes simplex virus thymidine kinase promoter (Vegeto et al., 69 *Cell* supra)). Both reporter plasmids were digested with XhoI and HindIII restriction enzymes and a 6.7 Kb fragment from MMTV-LUC and a 0.12 Kb fragment from PRE$_2$tk-CAT were isolated and ligated, resulting in a plasmid called PRE$_2$tk-LUC.

For the construction of TAT2950-LUC, pTATCAT, a plasmid containing the 2950 base fragment of the TAT gene promoter sequence (available from Dr. Gunther Schutz, University of Heidelberg, Germany), and the MMTV-LUC plasmid were digested with SacI and XhoI restriction enzymes, respectively, blunt-ended with T4 DNA polymerase and then digested with HindIII restriction enzyme.

The 2.9 Kb fragment resulting from the digestion of the pTAT-CAT plasmid, and the 6.7 Kb fragment, containing the luciferase gene and the backbone resulting from MMTV-LUC digestion products, were ligated to create the plasmid TAT2950-LUC.

Cell Culture

Monkey kidney CV-1 fibroblasts and human endometrial HeLa cells (ATCC, Rockville, Md.) were routinely maintained in Dulbecco's modified Eagle's medium (DMEM) (Biowittaker, Md.) supplemented with 10% fetal bovine serum (FBS, obtained from Hyclone Laboratories, Utah). Human hepatoma HepG2 cells (ATCC) were maintained in Eagle's Minimal Essential Medium (MEM) containing 10% FBS.

Transient Transfection Assays

Cells were seeded in 12-well, 96-well or 10 cm tissue culture plates. DNA was introduced into cells using calcium phosphate co-precipitation as described in Berger et al., 41 *J. Steroid Biochem. Mol. Biol.* 733 (1992). 20 µg of DNA/ml of transfection buffer were used in each transfection reaction. In this mix, the concentration of the luciferase plasmids and that of the internal control plasmid pCH110 (Pharmacia, Inc.), which contains the gene for the β-galactosidase enzyme, remained constant (5 g of each plasmid DNA), while the receptor plasmid concentration varied as indicated for each experiment. Different amounts of receptor parental plasmid, pSV2-neo (Dr. Bert O'Malley, Baylor College of Medicine, Houston, Tex.) was included to keep constant the total amount of the SV40 enhancer vectors. pGEM4 plasmid DNA (Promega Biotech, Madison, Wis.) was added to balance the total DNA concentration to 20 g/reaction. For the 96-well plate experiments, transfections were performed on a Biomek 1000 Automated Laboratory Workstation (Beckman Instruments, Fullerton, Calif.).

Cells were seeded 24 hours prior to transfection in the flat-bottom tissue culture plates ($5 \times 10^{-3}$ cells/well) in phenol red-free DMEM containing 10% FCS. Plasmid DNA was diluted in 1 ml of 1 mM Tris, pH 7.4, 0.1 mM EDTA, 0.25M $CaCl_2$. Using calcium phosphate co-precipitation, DNA solution was added dropwise with vortexing into an equal volume of 2X HBS pH 6.9 (280 mM NaCl. 50 mM HEPES, 1.5 mM $Na_2HPO_4$) and precipitates were allowed to form for 20 minutes. Cells were transfected ( 11 ml of DNA mix/well) for 6 hours and then washed with phosphate-buffered saline (PBS) to remove the precipitate. Cells were incubated for an additional 24 hours in phenol red-free medium containing 10% charcoal-treated FCS, with or without hormones as indicated in the text. Cell extracts were prepared as described by Berger et al., Supra, and assayed for luciferase and β-galactosidase activities. All determinations were performed in triplicates in at least two independent experiments, and were normalized for transfection efficiency by using β-galactosidase as an internal control.

EXAMPLE 1

Differential Transcriptional Activity of PR-A and PR-B

In order to define the activities of the human progesterone receptor isoforms A (PR-A) and B (PR-B), the expression vectors phPR-A and phPR-B, that encode exclusively either PR-A or PR-B, were transiently transfected into either CV-1, HeLa or HepG2 cells together with the progesterone responsive MMTV-Luciferase reporter (MMTV-LUC). The cells were then incubated with either progesterone or an inert vehicle (ethanol (ETOH)). Western immunoblot analysis using two PR specific monoclonal antibodies (B30 and AB52, available from Dean Edwards, University of Colorado) confirmed that no hPR-A was synthesized from our PR-B constructs.

Figure 2A:
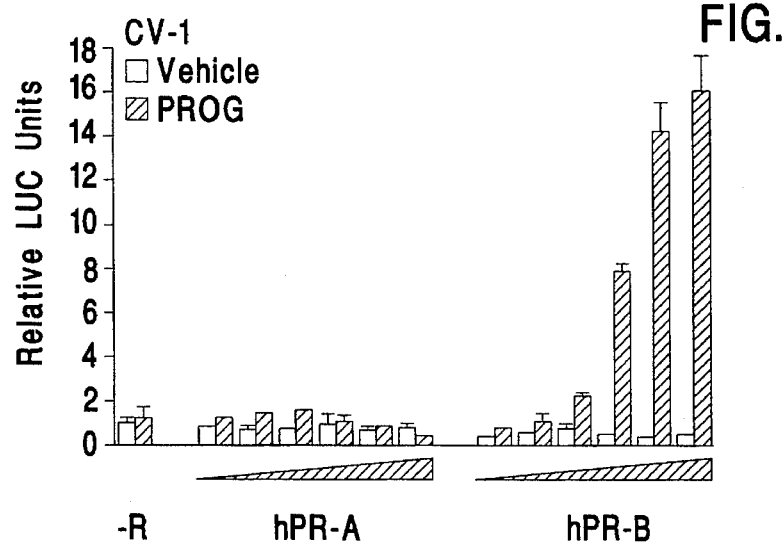
FIGS. 2A–2C are a series of graphs showing increasing amounts of the phPR-A or phPR-B plasmid DNA (0.05, 0.1, 0.25, 0.5, 2.5, and 5 g) together with 5 g/ml of the MMTV-LUC reporter DNA and 5 g/ml of pCH110 (an SV40-β-galactosidase expression vector) as an internal control, that were transiently transfected into CV-1 (FIG. 2A), HeLa (FIG. 2B) or HepG2 (FIG. 2C) cell lines as described in the Experimental Procedures. Cells were treated with an inert vehicle (ethanol (ETOH) or with $10^{-7}M$ progesterone as indicated for 24 hours and assayed for β-galactosidase and luciferase activity (LUC activity was normalized for β-galactosidase activity.) The relative luciferase activity is calculated by dividing the normalized luciferase at a given point by that obtained in the absence of transfected receptor or ligand. Expression of PR-A or PR-B had no direct effect on SV40 driven β-galactosidase activity. Data shown indicate the mean +/− the average deviation from the mean of triplicate estimations. -R shows transcriptional activity in the absence of any transfected receptor.

In CV-1 cells, the endogenous level of PR is low. As a result, there was no significant hormone dependent activation of the MMTV promoter in the absence of transfected receptor (-R) (FIG. 2A). Transfection of increasing amounts of the phPR-B expression vector permitted progesterone mediated activation of the MMTV promoter, the degree of which was proportional to the input plasmid. In contrast, in the same cell background, no progesterone-induced activation of the MMTV promoter by PR-A was observed. These results indicated that progesterone-induced activation of the MMTV promoter was regulated differentially by PR-A and PR-B.

Figure 2B:
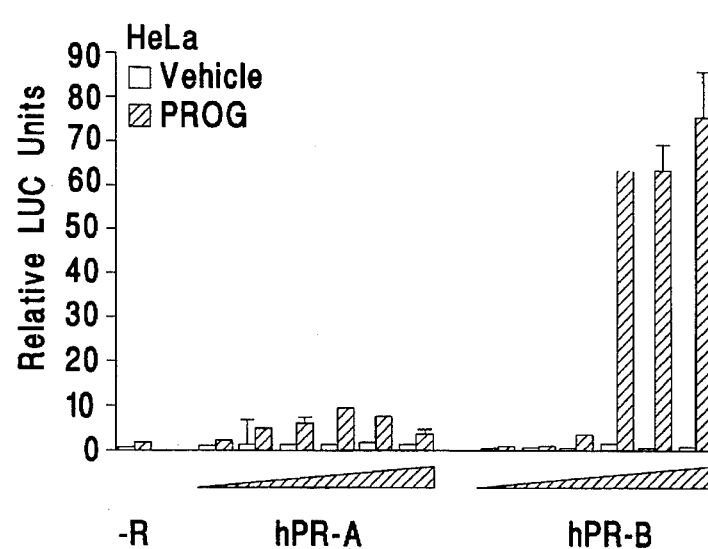
Figure 2C:
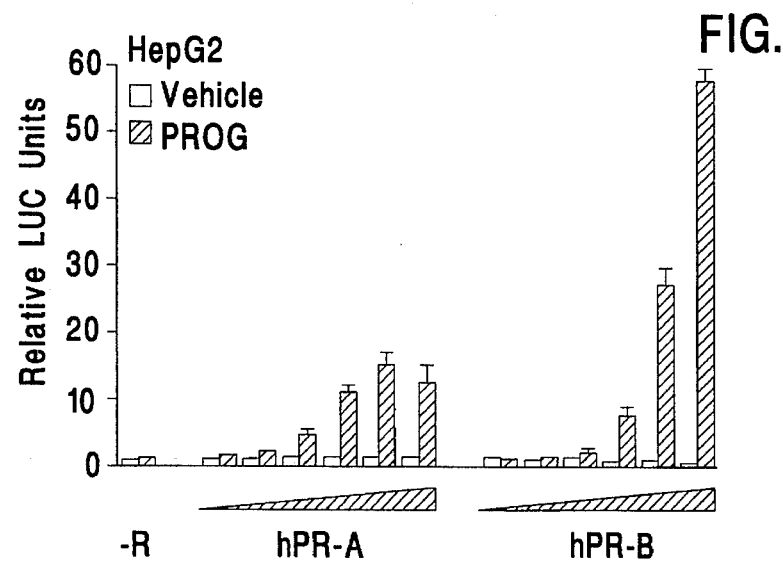

The influence of cell-type on PR isoform-specific activation of MMTV was evaluated by performing additional co-transfection experiments in HeLa (FIG. 2B) and HepG2 cells (FIG. 2C). Interestingly, PR-A was transcriptionally active on this promoter in HeLa cells, where its efficacy was 15% that of PR-B, reaching a maximal ten-fold induction at 250 ng of transfected DNA (FIG. 2B). A similar transcription assay performed in the HepG2 cell line revealed that in this cell line both PR-A and PR-B functioned as efficient activators of the MMTV promoter (FIG. 2C).

To eliminate the possibility that the differential regulatory activity of the two PR isoforms was an artifact of their expression level in the cells, hormone binding analysis of extracts prepared from transfected CV-1 cells were performed according to the procedure described in Berger et al., supra. The expression levels of PR-A and PR-B were determined to be 178 fmoles/mg and 35 fmoles/mg respectively, indicating that PR-A was expressed at approximately 5 times greater concentration than PR-B in CV-1 cells. Repeated experiments in the other cell lines showed no more than 20% variation in receptor levels of PR-A and PR-B. Furthermore, immunoblot analysis confirmed the expression of intact receptors of the correct molecular weight, and that no detectable PR-A was produced by the PR-B expression plasmid. Therefore, cell context influences PR-A and PR-B mediated activation of the MMTV promoter.

EXAMPLE 2

Dominant Negative Effect of PR-A on PR-B

Having shown that PR-A and PR-B have distinct cell-specific activities when assayed individually on the MMTV promoter, the potential modulatory effect of PR-A or PR-B was examined. Specifically, CV-1, HeLa and HepG2 cells were transiently transfected with phPR-B and increasing amounts of phPR-A, and PR-B activity was assayed in the presence of increasing concentrations of PR-A when incubated with progesterone or the ETOH inert vehicle.

Figure 3A:
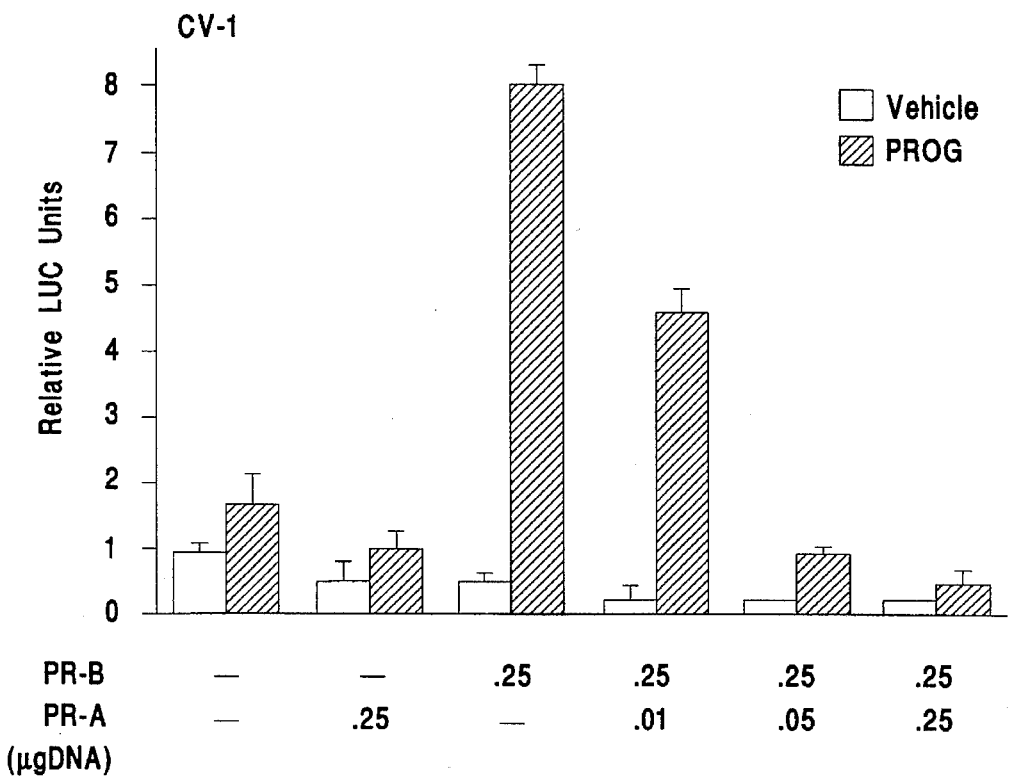
FIGS 3A–3B are a series of graphs showing CV-1 (FIG. 3A) or HeLa (FIG. 3B) cells that were transiently transfected with either 0.25 g of phPR-A or 0.25 g phPR-B alone, or 0.25 g phPR-B in the presence of increasing concentration of phPR-A together with 5 g of the MMTV-LUC reporter and 5 g of pCH110 as an internal control. Cells were treated with an inert vehicle (ETOH) or with $10^{-7}$M progesterone as indicated for 24 hours and assayed for β-galactosidase and luciferase activity (LUC activity was normalized for β-galactosidase activity). The relative luciferase activity is calculated by dividing the normalized luciferase value at a given point by that obtained in the absence of transfected receptor or ligand. Data shown indicate the mean +/− average deviation from the mean of triplicate estimations.

In CV-1 cells, PR-B but not PR-A allowed hormone dependent regulation of the MMTV promoter (FIG. 3A). Surprisingly, the progesterone-dependent activation obtained when equal amounts of phPR-A and phPR-B expression vectors were transfected into these cells was only 7% that of PR-B alone (FIG. 3A). Decreasing the concentration of PR-A restored the PR-B-dependent, progesterone-induced transcriptional activity such that at PR-A/PR-B DNA ratios of 1:5 or 1:25 the recovery of PR-B mediated transcription was 13% and 57%, respectively. Even at the lowest concentration of phPR-A transfected there was a strong reduction in PR-B activity. The progesterone concentration required for half maximal inhibition was $10^{-8}$M, a concentration that corresponds to the affinity of the receptor for ligand. The efficiency of this repression revealed a dominant negative role of PR-A in the progesterone mediated regulation of MMTV transcription in CV-1 cells.

Figure 3B:
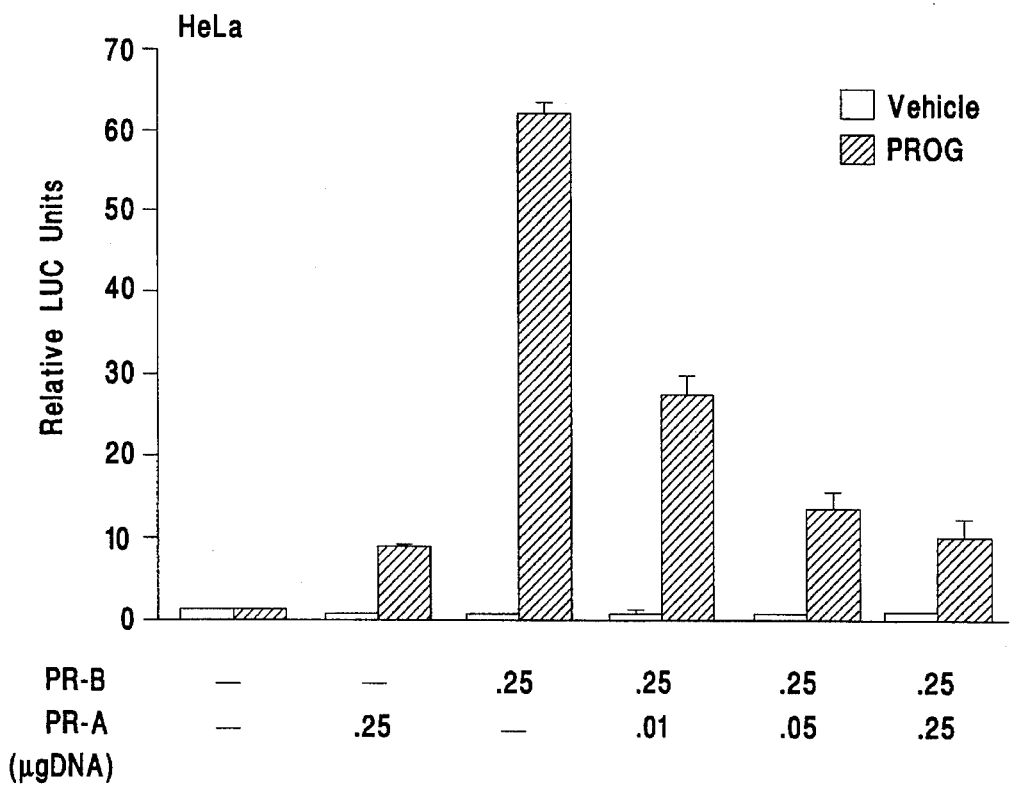

Next, the role of PR-A as a repressor of PR-B activated MMTV promoter transcription in HeLa cells, where PR-A was found to be minimally active, was evaluated. As shown in FIG. 3B, the transcriptional repression was 84%, 78% and 56% at 1:1, 1:5, 1:25 PR-A/PR-B DNA ratios, respectively, confirming that PR-A mediated inhibition of PR-B activity correlated with the inability of PR-A to transactivate. As expected, coexpression of PR-A and PR-B in HepG2 cells, where these receptor isoforms were shown to be independently active (See FIG. 2C), resulted in an overall additive effect of the co-expressed receptors on MMTV transcription (data not shown).

To eliminate the possibility that inhibition of PR-B activity was due to an alteration of the levels of the individual expressed isoforms, a Western immunoblot and in vitro hormone binding analysis on extracts prepared from transfected CV-1 cells was performed. The results indicated that coexpression of PR-A and PR-B using SV-40 based expression plasmids did not alter the level of either receptor. Reproducibly, PR-A was expressed about 3–5 times greater than PR-B. Therefore, equimolar concentrations of PR-A and PR-B results in greater than 90% inhibition of MMTV-LUC transcriptional activity in CV-1 cells. In addition, identical results were obtained when using receptor expression vectors that utilized a Rous Sarcoma Virus promoter in place of the SV-40 promoter (i.e., pRST7hPR-A and pRST7hPR-B ). This indicates that the effects of PR-A are not peculiar to the particular expression system used. Furthermore, this Example shows that, in addition to its accepted role as a transcriptional activator, PR-A acts as a hormone-dependent transdominant repressor of PR-B function in contexts where PR-A activity is minimal or absent.

EXAMPLE 3

Promoter Specificity of the Dominant Negative Effect of PR-A

Figure 4A:
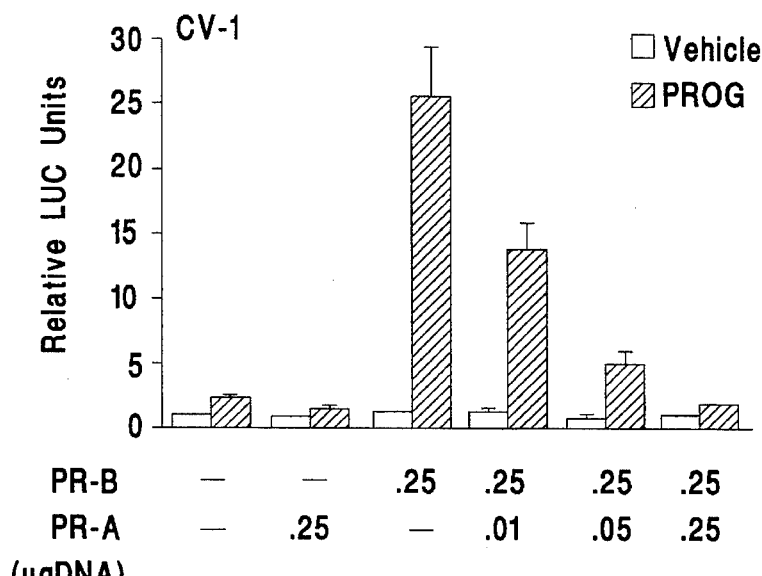
FIGS. 4A–4B are a series of graphs showing CV-1 (FIG. 3A) or HepG2 (FIG. 4B) cells that were transiently transfected with either 0.25 g/ml of phPR-B or phPR-A alone, or phPR-B in the presence of increasing concentrations of phPR-A, together with 5 g/ml of the $PRE_2$tk-LUC reporter and 5 g/ml of pCH110 as an internal control. HeLa cells (FIG. 4C) were transfected with either phPR-B or phPR-A together with 5 g/ml of the pTAT2950 reporter and 5 g/ml of pCH110 as an internal control. Cells were treated with an inert vehicle (ETOH) or with $10^{-7}$M progesterone for 24 hours, and assayed for luciferase and β-galactosidase activity. The relative luciferase activity is calculated by dividing the normalized luciferase value at a given point by that obtained in the absence of transfected receptor or ligand. The data shown represent the mean +/− average deviation from the mean of triplicate estimations.

To determine if inhibition of transcription by PR-A was a general phenomenon, or was restricted to the MMTV promoter, PR-A and PR-B function was evaluated on other progesterone receptor responsive promoters. In one instance, $PRE_2tk$-LUC reporter plasmid, which contains 2 copies of a progesterone response element (PRE) linked to the thymidine kinase (tk) promoter, was utilized. In CV-1 cells, PR-B was transcriptionally active whereas PR-A was transcriptionally inactive (FIG. 4A). When phPR-B was transfected together with phPR-A, we observed a repression of PR-B activity, similar to that observed on the MMTV promoter. This demonstrated that PR-A mediated repression of PR-B function in CV-1 cells is not promoter specific. Further, similar results were obtained when the same experiment was performed in HeLa cells (data not shown). In contrast, when the identical promoter and receptor combinations were assayed in HepG2 cells, PR-A was found to be an activator of transcription and had no effect on PR-B transcriptional activity (FIG. 4B), similar to what was observed using the MMTV promoter (See FIG. 2C).

Together, these data suggested that PR-A-specific down-regulation of transcription extended to other progesterone responsive promoters while maintaining cell specificity.

Figure 4B:
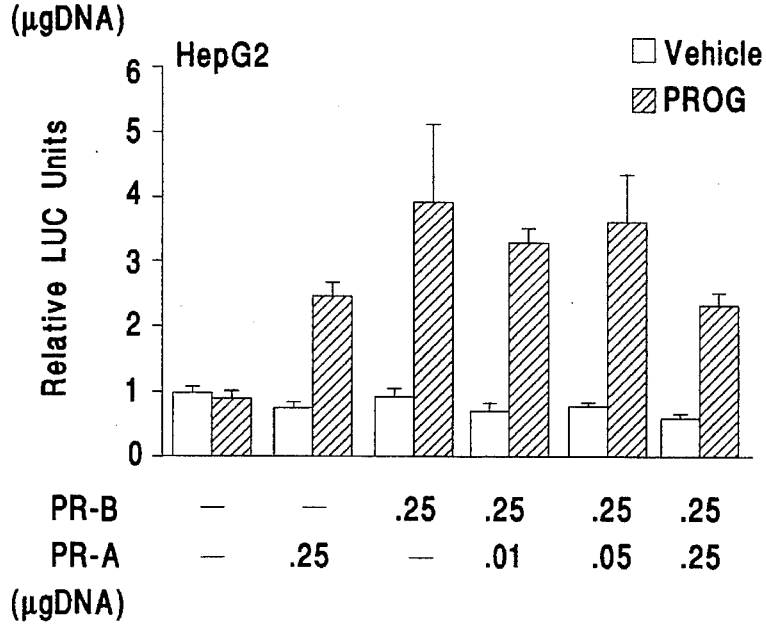
Figure 4C:
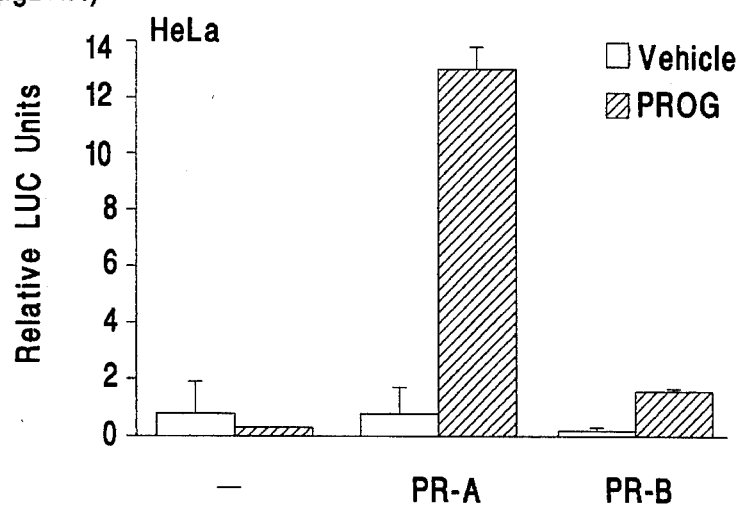

It was important to assess whether PR-A was inactive on all progesterone responsive promoters in CV-1 and HeLa cells. To address this issue the progesterone responsive tyrosine amino transferase (TAT) promoter (available from Dr. Gunther Schutz, University of Heidelberg, Germany) was utilized. Significantly, in HeLa cells PR-A, but not PR-B, functioned as a hormone dependent regulator of the TAT promoter (FIG. 4C). At the disclosed concentration of expressed receptor, PR-A promoted a 10-fold induction of TAT promoter activity. Thus, PR-A was not a general repressor of PR-B mediated transcription in HeLa cells, but rather inhibited transcription in a promoter-specific manner. In addition, in this cellular context PR-B is not an inhibitor of PR-A function, attesting to the specific function of PR-A as a transcriptional repressor.

Further analysis of TAT promoter regulation revealed that it responded to progesterone in HepG2 cells, following transfection of either phPR-A or phPR-B (data not shown). In CV-1 cells the TAT promoter was unresponsive to either receptor subtype (data not shown).

EXAMPLE 4

Dominant Negative Effects of PR-A on GR Function

The MMTV promoter has been shown to respond to glucocorticoids. Cato et at., 7 *EMBO J* 1403 (1988); Stahle et al., 84 *P.N.A.S. U.S.A.* 7871 (1987). Therefore, the potential antagonist effects of PR-A on glucocorticoid receptor (GR) mediated response was examined by establishing a GR responsive MMTV transcription unit in transfected CV-1 cells. HeLa cells were not used for this example, as they contain a high level of endogenous GR.

Figure 5A:
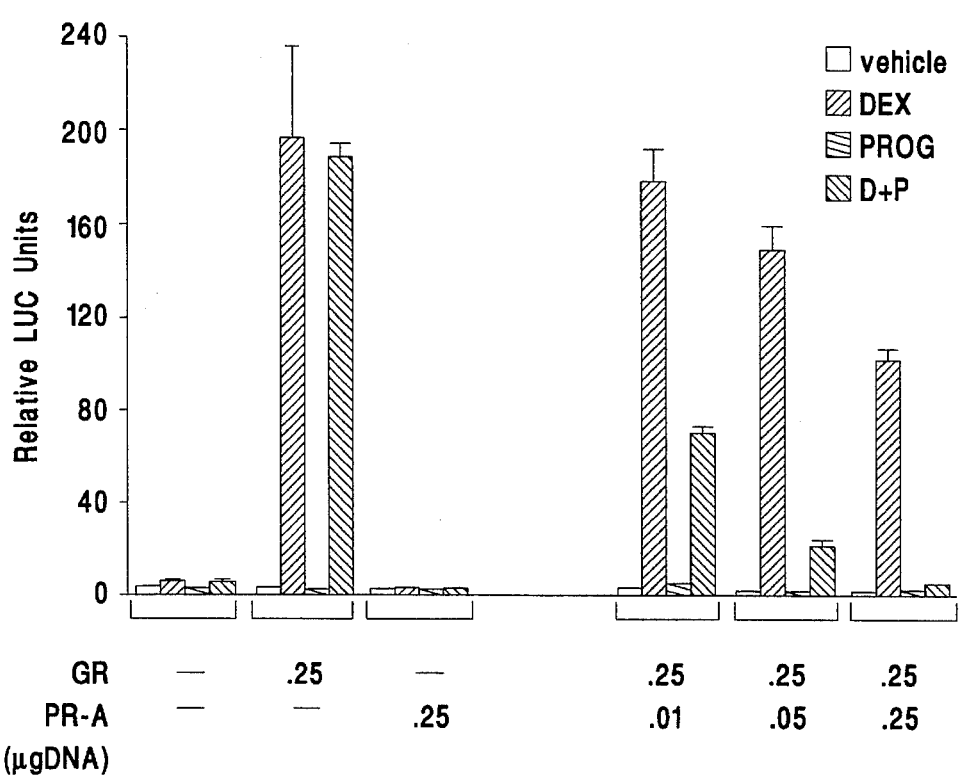
FIGS. 5A–5B are a series of graphs showing CV-1 cells that were transiently transfected with either pRShGR, phPR-A, phPR-B, or pRShGR in the presence of increasing concentrations of phPR-A (FIG. 5A), or pRShGR in the presence of increasing concentrations of phPR-B (FIG. 5B). In addition 5 g/ml of MMTV-LUC and 5 g/ml of pCH110 were included in all transfections. Cell cultures were treated with an inert vehicle (ETOH), $10^{-7}$M dexamethasone (DEX), progesterone (PROG) or DEX and PROG for 24 hours and assayed for luciferase and β-galactosidase activity. The data shown are the mean values +/− the average deviation from the mean of triplicate determinations.

Specifically, an expression vector encoding GR (pRShGR) was transfected into CV-1 cells together with the MMTV-LUC reporter. Half maximal activation of MMTV by dexamethasone-activated GR occurred at 250 ng of transfected DNA (data not shown). In subsequent experiments a constant amount (250 ng) of GR expression vector was transfected with equimolar or decreasing amounts of phPR-A DNA together with the MMTV reporter (FIG. 5A). Transcriptional activity was measured following four different hormonal stimuli; ETOH vehicle alone, dexamethasone, progesterone, or dexamethasone plus progesterone. This allowed for the independent measurement of receptor-specific responses at each different receptor ratio.

As shown in FIG. 5A, there was negligible hormone-dependent induction of transcription in cells transfected with an "empty" control vector, representing most likely the transcriptional activity of a low level of endogenous GR. When GR was transfected alone, a 450-fold induction of MMTV promoter activity was detected in the presence of dexamethasone or in the presence of dexamethasone and progesterone in combination. In this context PR-A was minimally active on its own. Interestingly, in the absence of progesterone, PR-A decreased the dexamethasone induction of GR activity to about 53% of control levels. Hormone-independent transcriptional interference was less apparent at lower concentrations of receptor suggesting most likely that this activity related to an over-expression of PR-A. In the presence of progesterone and dexamethasone, GR activity decreased dramatically to 2% of induced control levels.

Even at the lowest concentration of PR-A (0.01 µg), we observed a significant hormone-dependent inhibition of GR function.

Figure 5B:
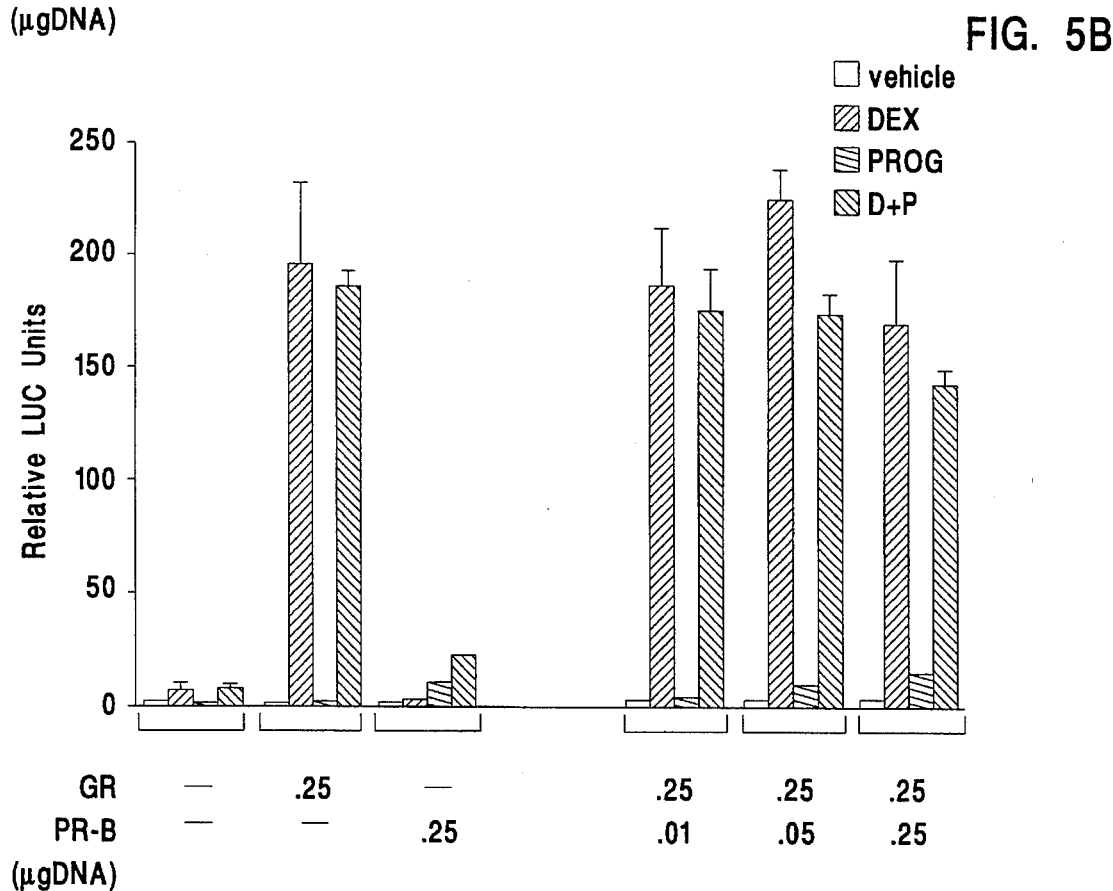

To determine the specificity of PR-A mediated repression of GR function in this cell and promoter context, a similar assay was performed in the presence of PR-B (FIG. 5B). Vectors expressing PR-B (phPR-B) and GR (pRShGR) were cotransfected into CV-1 cells with the MMTV-LUC reporter and receptor activity was assayed under the same conditions as described above. Interestingly, as shown in FIGS. 5A and 5B, GR-mediated activation of MMTV promoter activity was about 10 times greater than PR-B and 50 times greater than PR-A in this context. Therefore, if PR-A mediated repression was due solely to its ability to displace GR and occupy the response elements of the MMTV promoter with a less efficient activator, then PR-B should also decrease GR-activated transcription to a level corresponding to PR-B maximal activity. However, as shown in FIG. 4B, co-expression of PR-B had minimal effects on GR function under the conditions examined. Therefore, progesterone-mediated repression of MMTV transcription was specific for PR-A subtype, and the repression of GR was not a consequence of occupancy of the GRE by a less efficient transactivator.

EXAMPLE 5

Repressor Function of PR-A at Physiological Concentrations of Progesterone

Figure 6:
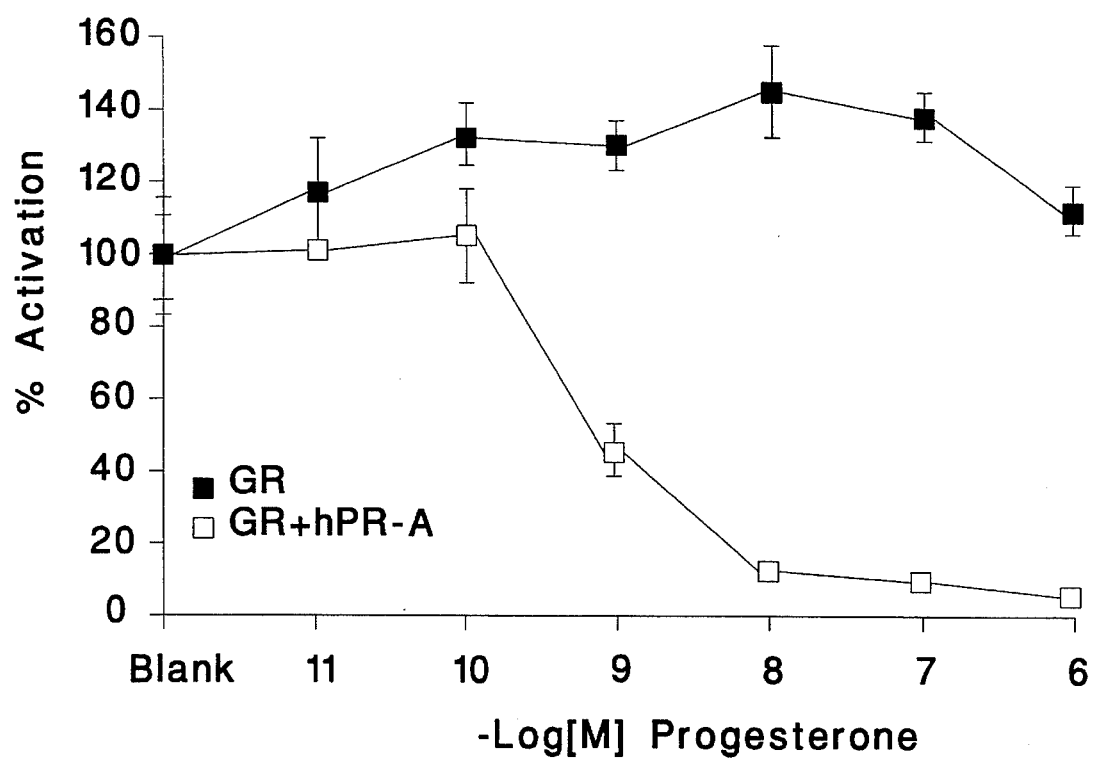
FIG. 6 is a graph showing CV-1 cells that were transiently transfected with either 0.25 g/ml pRShGR alone, or 0.25 g/ml pRShGR plus 0.05 g/ml phPR-A together with 5 g/ml of the MMTV-LUC reporter and 5 g/ml of the pCH110 as an internal control. The cells were incubated for 24 hours with $5 \times 10^{-8}$M dexamethasone and increasing concentrations of progesterone as indicated, and assayed for β-galactosidase and luciferase activity. The data are presented as percent (%) activation where the 100% value represents maximally activated GR in the presence of $10^{-8}$M dexamethasone alone (>450 normalized response). The data shown represent the means values +/− the coefficient of variation of quadruplicate estimations.

Next, the profile of inhibition with respect to progesterone concentration was defined using CV-1 cells transfected with MMTV-LUC and either GR alone, or GR in combination with phPR-A or phPR-B in the presence of $5 \times 10^{-8}$M dexamethasone and increasing concentrations of progesterone. As shown in FIG. 6, progesterone had no significant effect (12% increase) on GR activity when transfected alone. However, when GR and PR-A were transfected together, there was a 50% reduction in GR activity at $10^{-9}$M progesterone. This Example shows that PR-A activity as a repressor occurs at physiological concentrations of progesterone hormone.

EXAMPLE 6

PR-A is not a General Repressor of IR Transcriptional Activity

To analyze the specificity of PR-A action, we examined its ability to affect other receptor-dependent transcription systems. For this purpose, phPR-A was cotransfected with a vector expressing the vitamin D receptor (VDR) and assayed on a VDRE₂tk-LUC reporter (available from Dr. J. Wesley Pike, Ligand Pharmaceuticals, Inc.).

Figure 7:
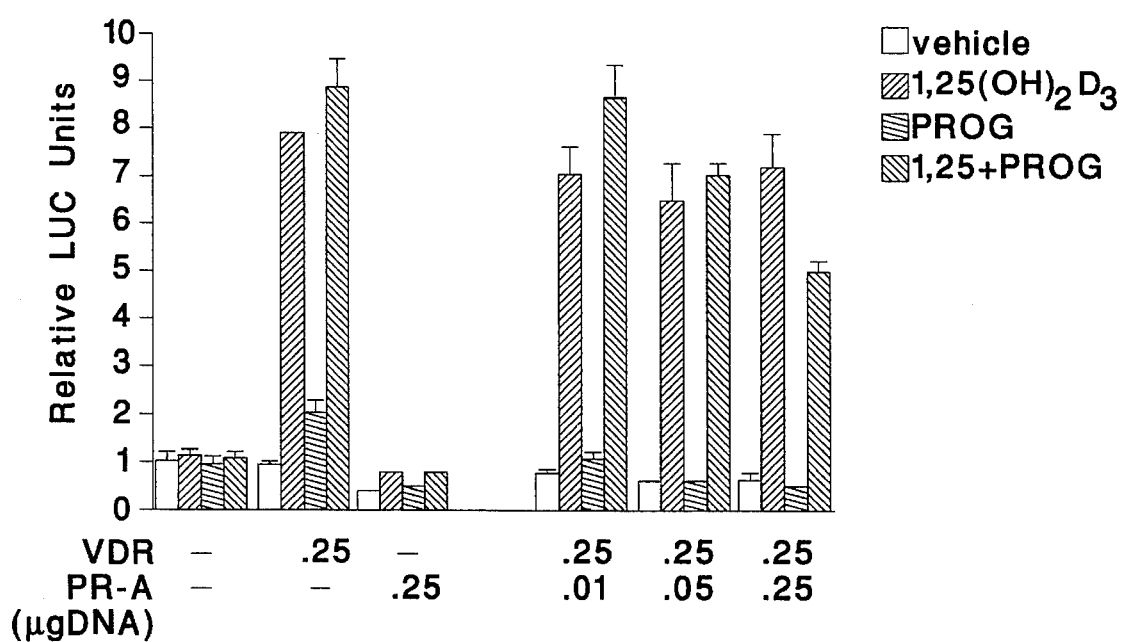
FIG. 7 is a graph showing CV-1 cells that were transiently transfected with either an expression vector producing the human vitamin D receptor (pRShVDR) or hPR-A alone, or with both vectors in combination. In addition the cells were transfected with 5 g/ml of the $VDRE_2$tk-LUC reporter plasmid and 5 g/ml of pCH110 as an internal control. Cells were treated with either an inert vehicle (ETOH), $10^{-7}$M $1,25(OH)_2 D_3$, progesterone or both hormones in combination as indicated. The data shown represent the mean value +/− the average deviation from the mean of triplicate determinations.

On a similar promoter containing two PRE sequences, PR-A functioned as a repressor of PR-B activity in CV-1 cells (See FIG. 4A). As shown in FIG. 7, hormone-dependent transactivation by VDR was not substantially affected by co-expression of PR-A either in the absence or presence of progesterone. The minor reduction noted at the higher concentrations of PR-A most likely related to non-specific "squelching" of a transcription factor required for both receptors, and is unlikely to relate to the function of PR-A. In addition, no effects of PR-A expression on the transcriptional activity of the SV-40 promoter (assayed as a fusion to β-galactosidase; data not shown) were observed. Thus, PR-A displays a selective role in the regulation of steroid IR transcriptional activity.

EXAMPLE 7

Repression of PR-B Function by PR-A Does Not Require DNA binding

To define more precisely the mechanism of PR-A mediated repression, the role of PR-A binding to DNA was measured. In particular, the ability of PR-A to repress GR transcriptional activation of MMTV-LUC in the presence of two dissimilar anti-progestins was evaluated. One compound, ZK112993 (Schering, A. G., Berlin, Germany), promotes the association of PR with DNA, whereas a second, ZK98299 (Schering, A. G.), interferes with DNA binding, possibly by preventing dimerization of the receptor. See, e.g., Klein-Hitpass et al., 19 *Nucl. Acids Res.* 1227 (1991); Takimoto et al., 89 *P.N.A.S.* 3050 (1992).

Figure 8A:
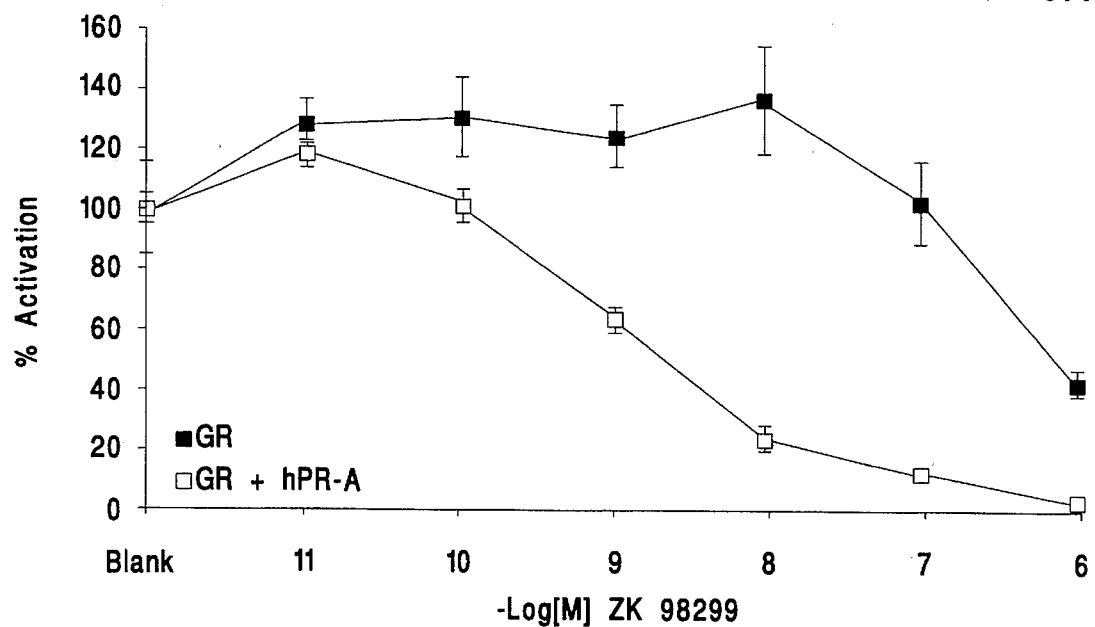
FIGS. 8A–8B are a series of graphs showing CV-1 cells that were transiently transfected with either pRShGR alone, or pRShGR plus phPR-A together with 5 g/ml of the MMTV-LUC reporter and 5 g/ml of pCH110 as an internal control. The cells were treated with $5 \times 10^{-8}$M dexamethasone and increasing concentrations of the antiprogestins (FIG. 8A) ZK98299 or (FIG. 8B) ZK112993 as indicated. The cells were harvested after 24 hours and the luciferase and β-galactosidase activities were measured. The results are presented as percent (%) activation, where 100% represents the maximal activity of GR in the presence of $10^{-8}$M dexamethasone (>450 fold normalized response). The data shown represent the mean +/− the coefficient of variation of quadruplicate estimations.
Figure 8B:
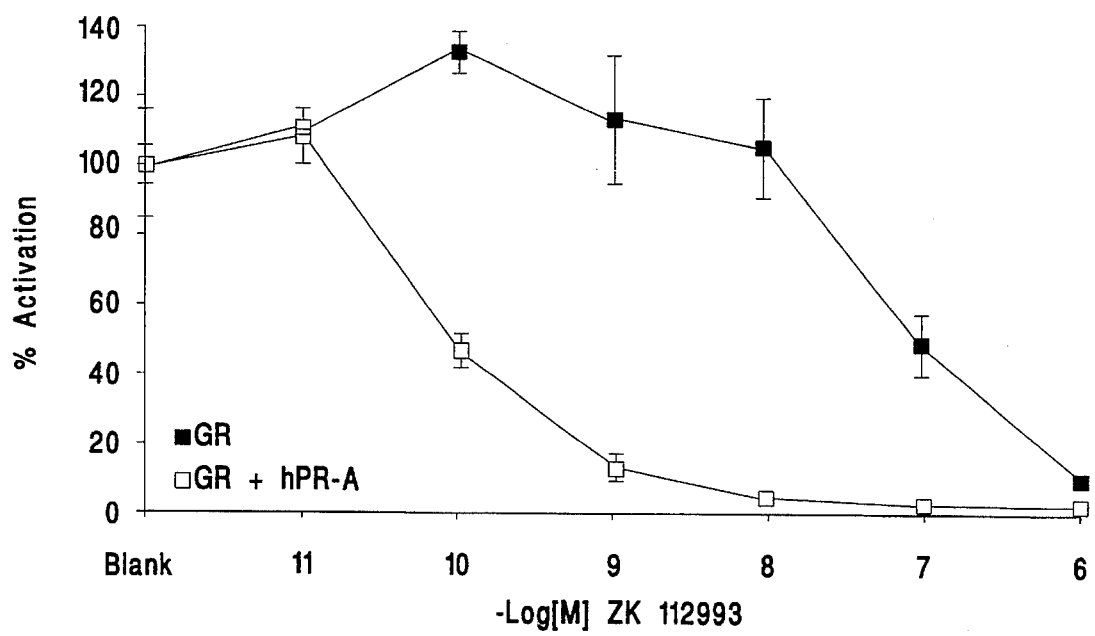

The effects of ZK112993 on CV-1 cells transfected with pRShGR and the MMTV-LUC reporter in combination with phPR-A, and in the presence of dexamethasone, were examined (FIG. 8B). At high concentrations, this compound directly inhibited GR function, but, co-introduction of PR-A, but not PR-B (data not shown), greatly potentiated this inhibition (>1000 fold), thereby suggesting that PR-A could function as a transcriptional repressor in the presence of either hormone agonists or antagonists. Further, this data shows that this class of compounds have the potential to function as potent anti-glucocorticoids in an indirect manner via PR-A.

This experiment was then repeated in the presence of ZK98299. As shown in FIG. 8A, ZK98299 also mediated an inhibition of GR function on the MMTV promoter via PR-A. Taken together, the results suggest that DNA binding may not be required for PR-A mediated repression of transcription.

Figure 9:
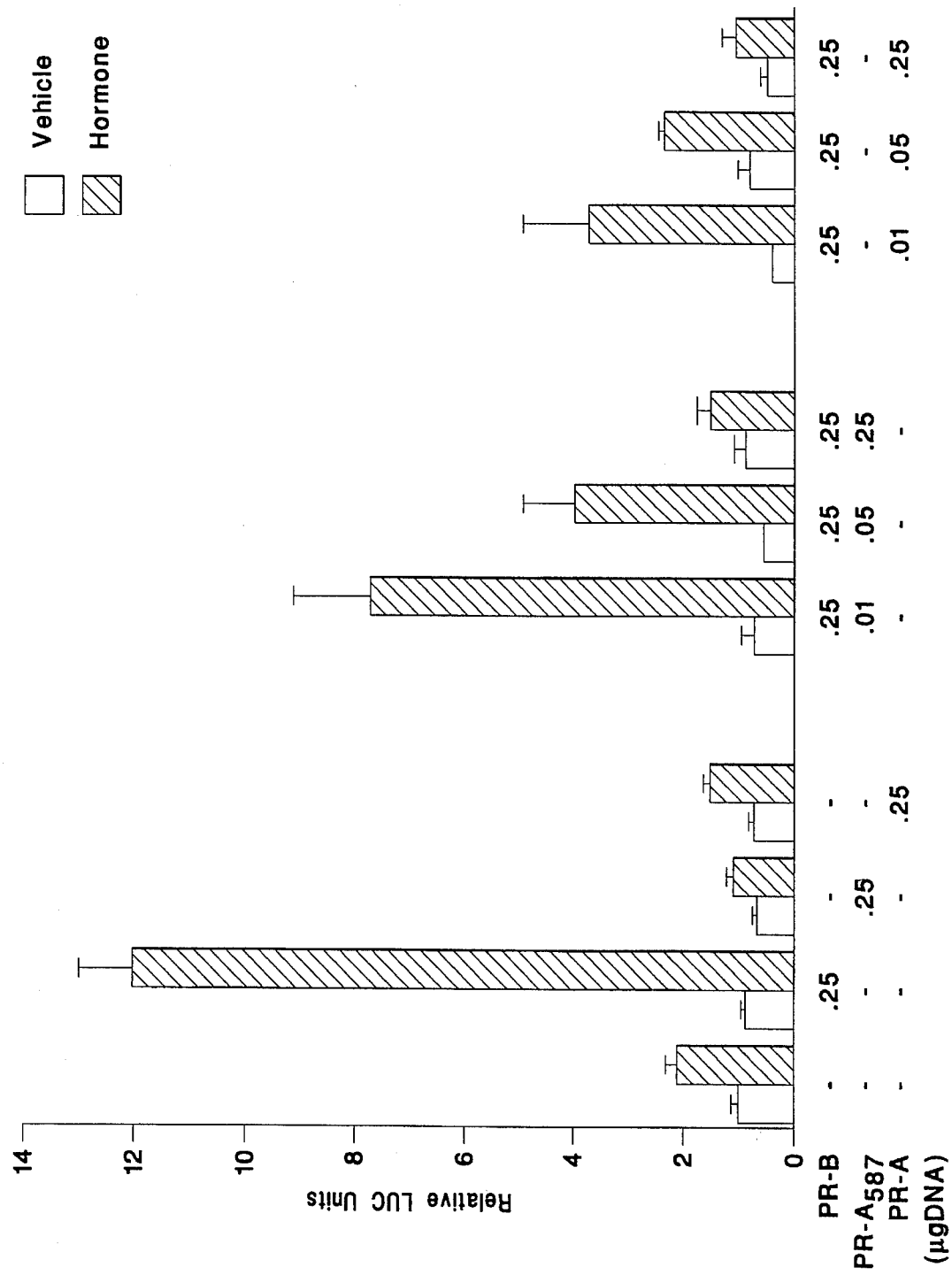
FIG. 9 is a graph showing CV-1 cells that were transiently transfected individually with either phPR-B, phPR-A587 or phPR-A alone, or with phPR-B in combination with increasing concentrations of phPR-A587 or phPR-A. In addition the cells were transfected with 5 g/ml of the MMTV-LUC reporter and 5 g/ml of pCH110 as an internal control. Cells were grown in the presence or absence of $10^{-7}$M progesterone for 24 hours. All values were normalized for transfection efficiency by simultaneous estimation of luciferase and β-galactosidase activities. The relative luciferase activity is calculated by dividing the normalized luciferase value at a given point by that obtained in the absence of transfected receptor or ligand. Data shown represent the mean +/− the average deviation from the mean of triplicate estimations.

To examine the issue of PR-A/DNA binding more directly, a mutant of PR-A, PR-A587, was utilized. In this mutant, two point-mutations were created in the DNA binding domain of PR-A, replacing the critical cysteine 587 residue with an alanine. The PR-A587 mutant was not capable of binding DNA in vitro, as demonstrated by gel-shift experiments, and was expressed at the same level as the wild type PR-A protein (data not shown). Results from the in vitro competition assay using this receptor mutant are reported in FIG. 9. The transcriptional activity of PR-B was reduced by 90% when equimolar amounts of phPR-A587 and phPR-B DNA were cotransfected into CV-1 cells. Therefore, the binding of PR-A to DNA is not an obligate step for the inhibitory activity of PR-A.

EXAMPLE 8

Modulation of AR and MR Activity by PR-A

The glucocorticoid (GR) and progesterone receptors (PR) are members of a sub-family of steroid receptors that also include the androgen receptor (AR) and the mineralocorticoid receptors (MR), all of which can bind to and operate through similar DNA regulatory sequences. Evans, R. M., 240 *Science* 889 (1988). To determine whether the activity of AR (vector pRShAR) or MR (vector pRShMR) could also be modulated by PR-A, we assayed their ability to activate the MMTV promoter after transfection in CV-1 cells in the presence of transfected phPR-A. This analysis was performed in the presence of either progesterone, the antiprogestins ZK112993, ZK98299, or an ETOH control vehicle.

Figure 10A:
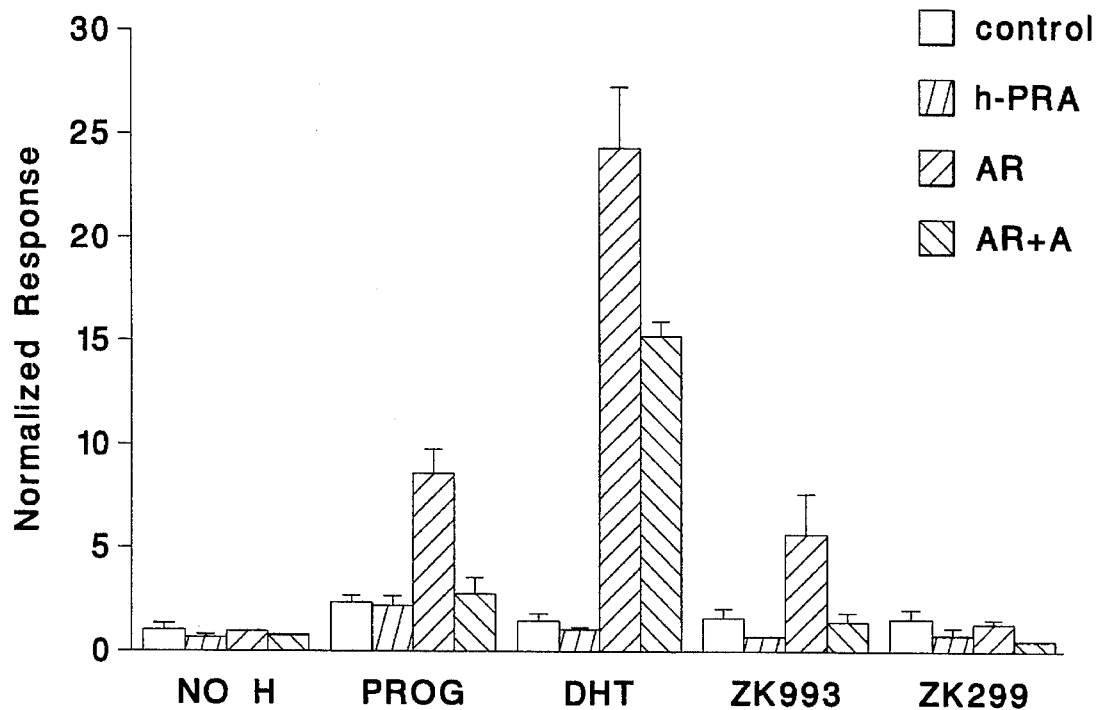
FIGS. 10A–10B are a series of graphs showing CV-1 cells that were transiently transfected with an expression vector for the human androgen receptor (pRShAR) alone, or in combination with phPR-A together with 5 g/ml of the MMTV-LUC reporter and 5 g/ml of pCH110 as an internal control.
Figure 10B:
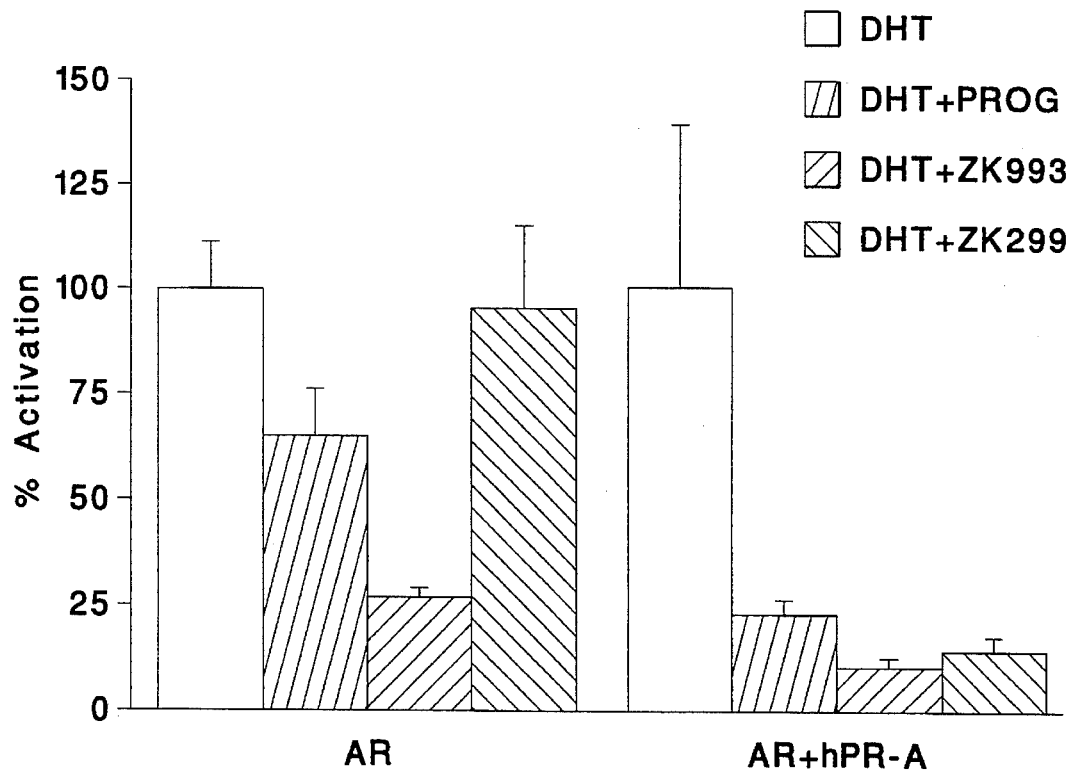

As shown in FIG. 10A, the activity of AR, as induced by dihydrotestosterone (DHT), was influenced directly by addition of progesterone. However, when AR activity was assayed in the presence of PR-A, the sensitivity of progesterone mediated inhibition was substantially increased (FIG. 10B). Surprisingly ZK112993 was an efficient inhibitor of DHT-activated AR. The efficacy of this antihormone (and potency, data not shown) was increased by the introduction of PR-A into the cells. Similarly, the antiprogestin ZK98299 had minimal direct effects on AR transcriptional activity, but the addition of PR-A to the cells increased this compound's sensitivity. This result reveals a mechanism whereby ZK98299, although having a low affinity for AR, could in this cell and promoter context, function as an efficient anti-androgen (FIG. 10B).

A similar series of experiments on transfected CV-1 cells were performed to examine the effect of PR-A on MR regulation of MMTV-LUC transcription, and showed that PR-A efficiently inhibits MR transcriptional activity in a hormone-dependent manner (data not shown). Cumulatively, these data suggest that PR-A is capable of inhibiting the transcriptional activity of all members of the steroid family of intracellular receptors.

EXAMPLE 9

Non-competitive Inhibition of ER Transcriptional Activity by Progesterone via PR-A CV-1 cells were transiently transfected with the reporter plasmid MMTV-ERE-LUC (available from Dr. Jon Rosen, Ligand Pharmaceuticals) and vectors producing human estrogen receptor (pRST7hER) alone as a control, or in combination with human progesterone receptor isoform PR-B (pSVhPR-B) or human progesterone receptor isoform PR-A (pSVhPR-A). Vegeto et al., supra. Cells were plated into 96-well tissue culture plates. The vector DNA was introduced into the CV-1 cells using calcium phosphate coprecipitation as described herein. More specifically, 20 µg of DNA/ml of transfection buffer were used in each transfection. Each transfection mix included 0.5 µg of pRST7hER, 9.5 µg of MMTV-ERE-LUC, 5 µg of pCH110 (which contains the gene for β-galactosidase) as an internal control and 5 µg of PGEM4 DNA as a carrier. Depending on the experiment, 0.1 µg pSVhPR-A or pSVhPR-B and an amount of pSVXV2neo (Dr. Bert O'Malley, Baylor College of Medicine) to bring the total amount of DNA to 20 µg was added. The concentration of pXVhPR-A vector chosen was determined by performing the experiment at several different concentrations of vector, and then using that concentration that was optimal for transcriptional readout. The concentration of pSVhPR-B vector was chosen based upon the amount required to give an identical amount of immunoreactive PR-A and PR-B. After transfections using a Biomek 1000 automated laboratory workstation, the cells were incubated with the precipitate for 6 hours. Cells were washed with PBS and incubated for 40 hours with or without hormones as indicated. Cell extracts were prepared as previously described herein and assayed for luciferase (LUC) and β-galactosidase activities. The Normalized LUC activity was calculated by dividing the raw luciferase ($\times 10^4$) units for each point by the β-galactosidase activity [(OD$_{415 nm}$×$10^5$)/time min.] at that point. The results of these experiments are shown in FIG. 11.

In this cellular system, ER responds appropriately to 17-β-estradiol demonstrating an EC$_{50}$ (effective concentration at 50% of maximal activation) of 3 nM and the activity of 17-β-estradiol on ER is unaffected by co-expression of either hPR-A or hPR-B (FIG. 11A). The ability of 17-β-estradiol to induce transcriptional activation by ER can be inhibited by addition of the pure anti-estrogen ICI-164,384 (Zenaca Pharmaceuticals, Macclesfield, England) (FIG. 11B). As expected, co-expression of hPR-A or hPR-B did not affect the activity of ICI-164,384. Interestingly, activation of ER by 17-β-estradiol can be inhibited by progesterone when ER and hPR-A are co-expressed (FIG. 11C). Maximal inhibition (55%) is achieved at 10 nM progesterone. This inhibition of ER function mediated by hPR-A is specific, as hPR-B will not inhibit under the same experimental conditions (FIG. 11D). Furthermore, hormone binding analysis indicated that equivalent levels of hPR-A and hPR-B were expressed in this system (data not shown). Together, these data indicate that progesterone can function as a partial ER antagonist in cells where hPR-A is co-expressed, and is inactive or minimally active. Importantly, this inhibition is mediated by a non-competitive mechanism, as no direct effects on ER were observed. Therefore, these experiments indicate that PR-A is a key modulator of steroid receptor function in the cell, and that the biological activity of progesterone goes beyond its ability to modulate PR function directly.

EXAMPLE 10

Non-competitive Inhibition of Estrogen Receptor Transcriptional Activity by Progesterone Antagonists CV-1 cells were transiently transfected with the reporter, plasmid MMTV-ERE-LUC and vectors producing human estrogen receptor (pRST7hER) alone, or with a vector producing the PR-A isoform of the human progesterone receptor (pSVhPR-A) as described in Example 9. The transcriptional activity of ER was measured following the addition of $10^{-7}$ M 17-β-estradiol alone, or in combination with the anti-progestins (A) RU486 (Roussel UCLAF, Paris, France), (B) ZK112993, or (C) ZK98299. The activity of ER in the presence of $10^{-7}$M 17-β-estradiol and $10^{-6}$M ICI-164,384 (a pure anti-estrogen) was used to determine the 100% inhibition value.

Figure 12A:
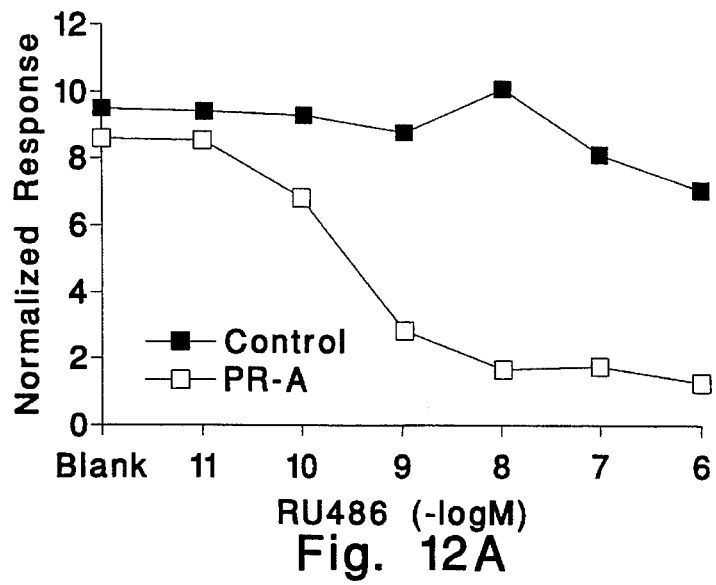
FIGS. 12A–12C are a series of graphs showing CV-1 cells that were transiently transfected with vectors expressing human estrogen receptor (pRST7hER) alone (Control), or in combination with a vector expressing human progesterone receptor isoform PR-A (pSVhPR-A), along with reporter plasmid MMTV-ERE-LUC. The transcriptional activity of the estrogen receptor in this experiment was measured following the addition of $10^{-7}$M 17-β-estradiol alone or in combination with the anti-progestins (FIG. 12A) RU486, (FIG. 12B) ZK112993 or (FIG. 12C) ZK 98299. The activity of estrogen receptor in the presence of $10^{-7}$M 17-β-estradiol and $10^{-6}$M ICI-164,384 (a pure anti-estrogen) was used to determine the 100% inhibition value. Experimental protocols and data calculation are as described in FIG. 11. The experiment detailed above is representative of independent assays (N>3). Data shown represent the mean +/− the average deviation from the mean of triplicate estimations. The average co-efficient of variation at each hormone concentration was less than 15%.
Figure 12B:
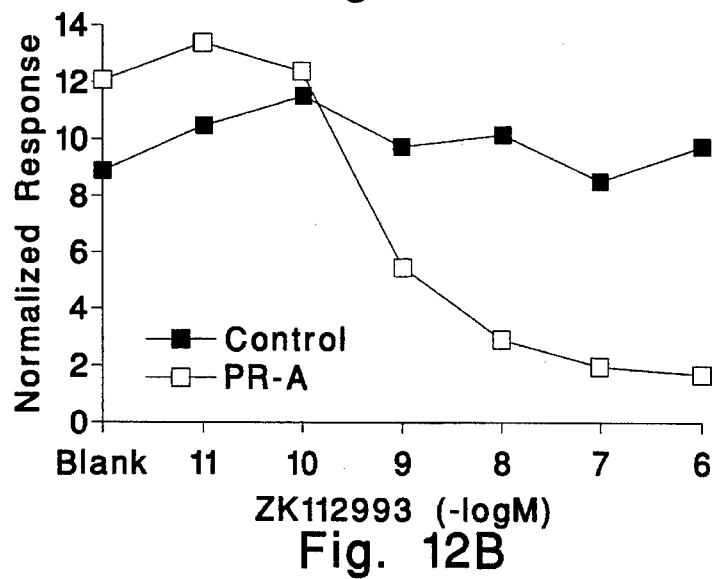
Figure 12C:
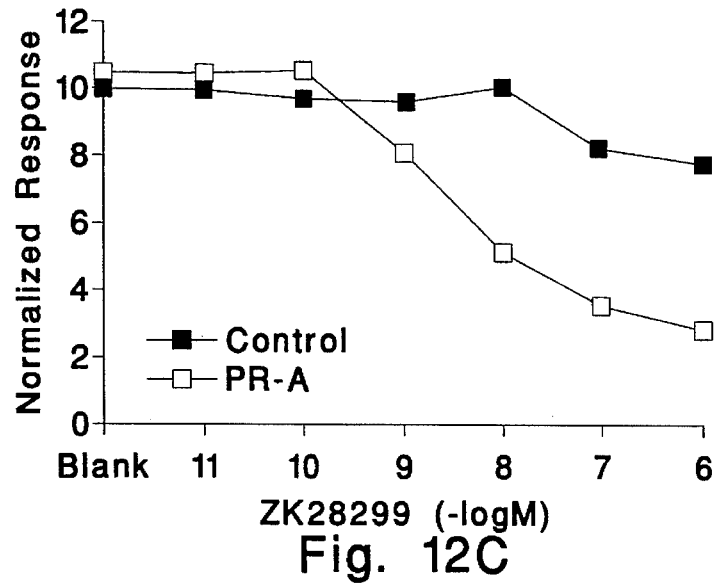
Figure 13A:
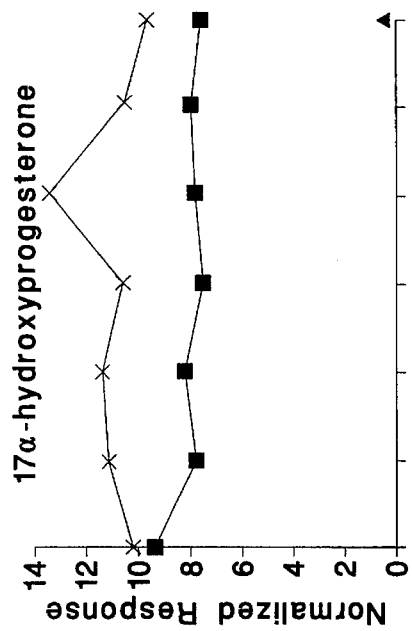
FIGS. 13A–13D are a series of graphs showing CV-1 cells that were transiently transfected with vectors expressing human estrogen receptor (pRST7hER) alone (Control (■), or in combination with a vector expressing the PR-A isoform (✖) of human progesterone receptor (pSVhPR-A), and the MMTV-ERE-LUC reporter plasmid as described for FIG. 12. The transcriptional activity of estrogen receptor was determined following the addition of $10^{-7}$M 17-β-estradiol alone or in combination with increasing concentrations of PR agonists (FIG. 13A) Norethynodrel, (FIG. 13B) 17-α-hydroxyprogesterone, (FIG. 13C) Norethindrone (FIG. 13D) Medroxyprogesterone acetate. The activity of estrogen receptor in the presence of $10^{-7}$M 17-β-estradiol and $10^{-6}$M ICI-164,384 (a pure anti-estrogen) was used to determine the 100% inhibition value (▲). The experimental protocol and data calculation are as described in FIG. 11. The experiment detailed above is representative of independent assays (N>3). Each data point was assayed in triplicate.
Figure 13B:
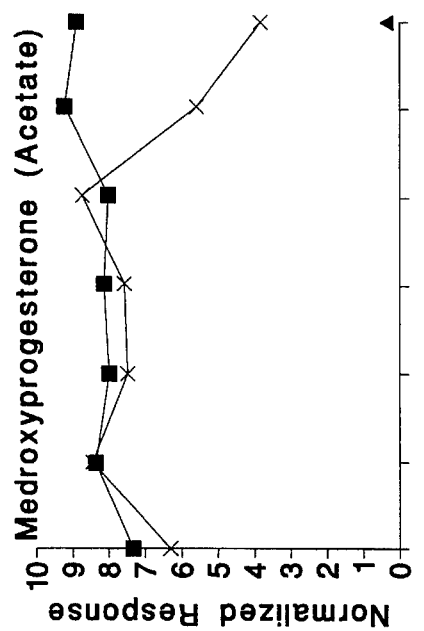
Figure 13C:
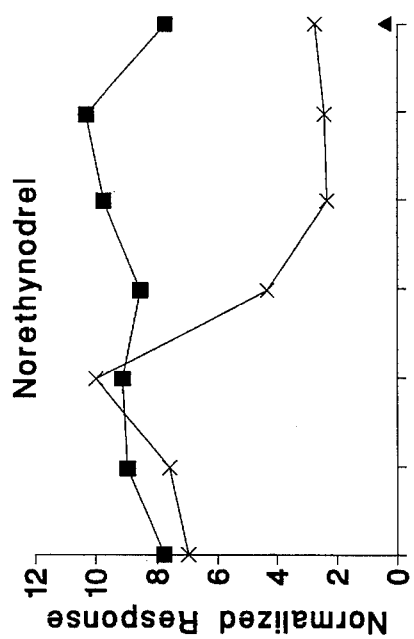
Figure 13D:
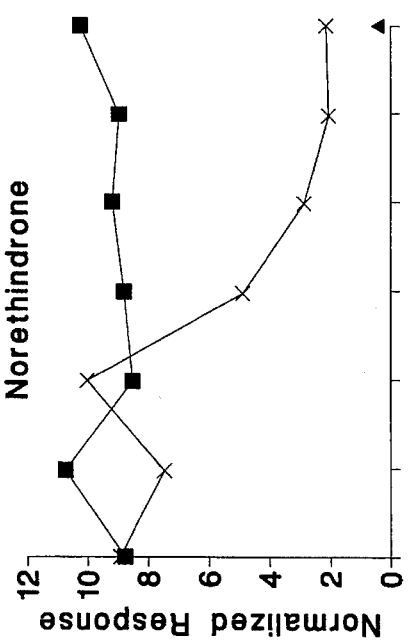

This Example was used to evaluate whether anti-progestins could modulate ER transcriptional activity through its interaction with co-expressed PR-A. In the absence or PR-A, none of the anti-progestin compounds tested exhibited any significant effects on ER activity (FIG. 12A–C). However, when PR-A was co-expressed in the cell, all three anti-progestins tested exhibited a potent anti-estrogenic activity. When compared to the activity of the pure anti-estrogen ICI-164,384, RU486 and ZK112993 each demonstrated greater than 80% efficacy (FIG. 12A & B). The compound ZK98299 was slightly less effective (70%) (FIG. 12C). The concentrations of anti-progestins required for half maximal inhibition (IC$_{50}$) of ER in the presence of hPR-A were 0.3 nM, 0.5 nM and 3 nM respectively for RU486, ZK112993 and ZK98299.

The ability of these compounds to inhibit the transcriptional activity of PR-B directly was also examined and it was found that RU486, ZK112993 and ZK98299 displayed IC$_{50}$ (50% maximal Inhibitory concentration) values of 0.5 nM, 0.6 nM and 2.7 nM respectively when measured in the presence of $10^{-8}$ progesterone. (In this experiment PR-B was used to evaluate progestin activity as we had determined previously that hPR-A is not an effective activator of transcription in CV-1 cells.) The value representing 100% inhibition is the transcriptional activity of PR-B in the absence of added progesterone. These results suggest that both processes; direct inhibition of PR and indirect inhibition of ER can occur simultaneously in the same cell upon administration of anti-progestins. In the presence of co-expressed PR-B and ER, the anti-progestins examined exhibited no anti-estrogenic activity (data now shown) confirming the specificity of this inhibition process.

EXAMPLE 11

Progesterone Receptor Agonists Differ in Non-competitive Inhibition of Estrogen Receptor Transcriptional Activity CV-1 cells were transiently transfected with the reporter plasmid, MMTV-ERE-LUC and vectors producing human estrogen receptor (pRST7hER) alone, or in combination with a vector producing the PR-A isoform of human progesterone receptor (pSVhPR-A) as described in Example 9. The transcriptional activity of ER was determined following the addition of $10^{-7}$M 17-β-estradiol alone, or in combination with increasing concentrations of the PR agonists (A) Norethynodrel, (B) 17-α-hydroxyprogesterone, (C) Norethindrone (D) Medroxyprogesterone acetate. The activity of ER in the presence of $10^{-7}$M 17-β-estradiol and $10^{-6}$M ICI 164,384 (a pure anti-estrogen) was used to determine the 100% inhibition value. The results of these experiments are shown in FIG. 13.

Interestingly, both Norethynodrel and Norethindrone, which are derived from 19-nor-testosterone are effective anti-estrogens in this assay (FIG. 13 A,C). Those compounds derived from hydroxy-progesterone; 17-α-hydroxy-progesterone and medroxyprogesterone acetate (MPA; PROVERA™) are considerably less effective (FIG. 13B, D). These data indicate that inhibition of ER activity may require less hormone activated PR than it takes to activate progesterone responsive promoters. Accordingly, a careful examination of the anti-estrogenic effects of progestin agonists in vivo should be held, particularly with respect to a determination of the tissue specificity of these responses.

EXAMPLE 12

Non-Competitive Anti-Estrogenic Activity of RU486 is not Promoter Restricted CV-1 cells were transiently transfected with vectors producing human estrogen receptor (pRST7hER) alone, or with a vector producing the PR-A isoform of human progesterone receptor (pSVhPR-A) and either the reporter plasmid ERE-TK-LUC or C3-LUC (available from Dr. Donald McDonnell, Ligand Pharmaceuticals). The experimental protocols and data calculation are as described in Example 8 with the exception that the MMTV-ERE-LUC reporter plasmid was replaced with either ERE-TK-LUC or C3-LUC. The transcriptional activity of ER on a (A) ERE-TK-LUC or C3-LUC (B) as assayed in the presence of absence of increasing concentrations of the anti-progestin RU486 are shown. The transcriptional activity of ER in the presence of $10^{-7}$M 17-β-estradiol and $10^{-6}$M ICI-164,384 (a pure anti-estrogen) was used to determine the 100% inhibition value.

Figure 14B:
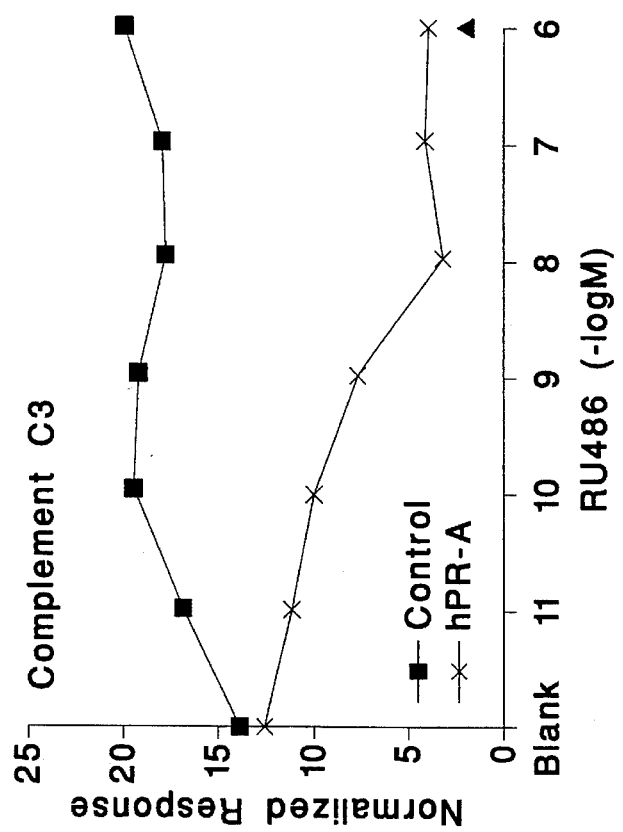
FIGS. 14A–14B are a series of graphs showing CV-1 cells that were transiently transfected with vectors expressing human estrogen receptor (pRST7hER) alone (Control), or in combination with a vector expressing the PR-A isoform of human progesterone receptor (pSVhPR-A). The transcriptional activity of estrogen receptor on a (FIG. 14A) synthetic ERE-TK-LUC plasmid or (FIG. 14B) a natural complement C3 promoter was assayed in the presence or absence of increasing concentrations of the anti-progestin RU486. The transcriptional activity of estrogen receptor in the presence of $10^{-7}$M 17-β-estradiol and $10^{-6}$M ICI-164,384 (a pure anti-estrogen) was used to determine the 100% inhibition value (▲). The experimental protocols and data calculation are as described in FIG. 11 with the exception that the MMTV-ERE-LUC reporter plasmid was replaced with either the ERE-TK-LUC or C3-LUC reporters plasmids. The experiment detailed above is representative of several independent assays. Each measurement was performed in triplicate.
Figure 14A:
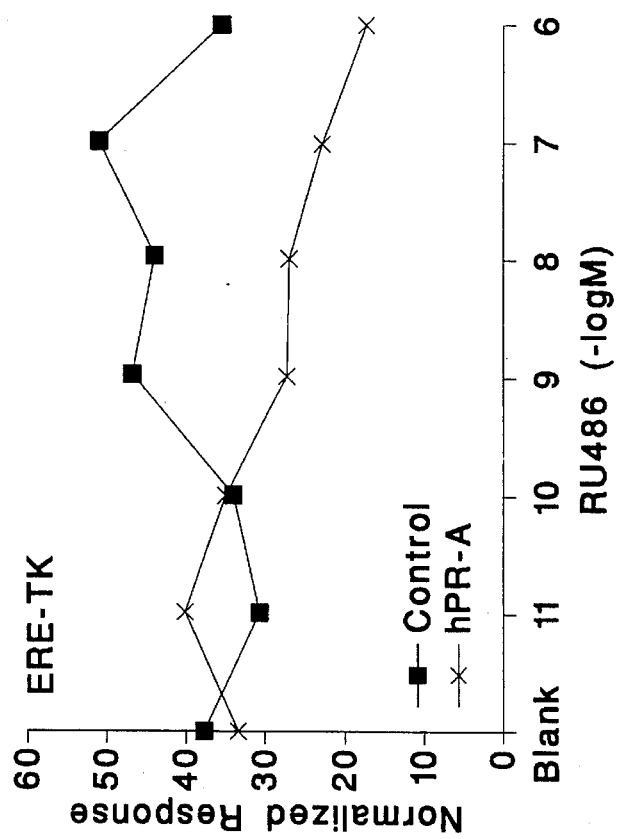

The results shown in FIG. 14 indicate that in the presence of co-expressed PR-A, in CV-1 cells, that RU486 effectively suppressed ER mediated activation of the synthetic ERE-TK-promoter (FIG. 14A) and the natural complement C3 promoter (C3-LUC) (FIG. 14B). As shown previously herein, PR-A can function as either a transcriptional activator or a repressor depending upon promoter and cell line examined. It is likely therefore that the ability of RU486 to function as antagonist of some, but not all estrogen-regulated responses is a consequence of the cell context of the target gene.

Furthermore, whether the anti-estrogenic effects of PR-A were similarly restricted by cell line, we examined the transcriptional activity of MMTV-ERE-LUC in HepG2 and HS578T (human breast cancer cell; ATCC), in the presence of the anti-progestins RU-486, ZK98299 and ZK112993 was examined. In HepG2 cells neither anti-progestin exhibited any anti-estrogenic activity, whereas in HS578T cells, both anti-progestins functioned as anti-estrogens (data not shown). The observation that the identical promoter is differentially regulated in different cell lines suggests that ER mediated activation of transcription is not identical in all cells. Since PR-A is not expressed in all tissues, these data suggest a novel mechanism to discover and generate specific estrogen antagonists.

While in accordance with the patent statutes, description of preferred reagents and conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

---

What is claimed is:

1. A method for screening for antagonists of steroid intracellular receptor-mediated transcription comprising:
   (a) introducing a first vector encoding asteroid intracellular receptor other than progesterone receptor and a second vector encoding progesterone receptor A form along with a third reporter vector into a cell in which the progesterone receptor A form is a negligible activator of transcription, wherein the reporter vector includes a gene encoding a reporter product and a promoter which is transcriptionally active in the presence of the steroid intracellular receptor and an activator of said steroid intracellular receptor-mediated transcription, but is a negligible activator of transcription in the presence of the progesterone receptor A form;
   (b) contacting the cell with the activator of steroid intracellular receptor-mediated transcription and a second compound; and
   (c) comparing the level of reporter product expressed in the cell relative to the level of reporter product expressed in a second cell containing the steroid intracellular receptor and reporter vector, and contacted with the activator and second compound, as an indication of the potential antagonist activity of the second compound on steroid intracellular receptor-mediated transcription.

2. The method of claim 1, wherein the steroid intracellular receptor is selected from the group consisting of androgen receptor, glucocorticoid receptor, mineralocorticoid receptor and estrogen receptor.

3. The method of claim 1, wherein the first and second cells are CV-1 cells or HeLa cells.

4. The method of claim 3, wherein the reporter vector comprises a gene encoding luciferase and the MMTV promoter.

5. The method of claim 1, wherein the steroid intracellular receptor is glucocorticoid receptor and the activator of steroid intracellular receptor-mediate transcription comprises a glucocorticoid receptor agonist.

6. The method of claim 5, wherein the glucocorticoid receptor agonist is dexamethasone.

7. The method of claim 1, further comprising, contacting a third cell containing a progesterone receptor isoform and a reporter vector with the second compound, wherein the progesterone receptor isoform is transcriptionally active in the third cell, and comparing the level of reporter product expressed in the third cell relative to the level of reporter product expressed in the third cell absent the progesterone receptor isoform.

8. The method of claim 7, wherein the second compound comprises an agonist of progesterone receptor.

9. The method of claim 7, wherein the third cell is a HepG2 cell and the reporter vector comprises a gene encoding luciferase and the MMTV promoter.

10. The method of claim 7, further comprising, contacting the third cell containing the progesterone receptor isoform and the reporter vector with an activator of progesterone receptor-mediated transcription and the second compound, and comparing the level of reporter product expressed in the third cell relative to the level of reporter product expressed in the third cell in the absence of the second compound.

11. The method of claim 10, wherein the second compound comprises an antagonist of progesterone receptor.

12. The method of claim 1, further comprising, contacting a third cell containing a progesterone receptor isoform and a reporter vector with an activator of progesterone receptor-mediated transcription and the second compound, wherein the progesterone receptor isoform is transcriptionally active in the third cell, and comparing the level of reporter product expressed in the third cell relative to the level of reporter product expressed in the third cell in the absence of the second compound.

13. The method of claim 12, wherein the second compound comprises an antagonist of progesterone receptor.

14. A method for screening for antagonists of steroid intracellular receptor-mediated transcription comprising:
   (a) providing a cell comprising asteroid intracellular receptor other than progesterone receptor, progesterone receptor A form and a reporter vector, wherein the progesterone receptor A form is a negligible activator of transcription in the cell, and wherein the reporter vector includes a gene encoding a reporter product and a promoter which is transcriptionally active in the presence of the steroid intracellular receptor and an activator of said steroid intracellular receptor-mediated transcription, but is a negligible activator of transcription in the presence of the progesterone receptor A form;
   (b) contacting the cell with the activator of steroid intracellular receptor-mediated transcription and a second compound; and
   (c) comparing the level of reporter product expressed in the cell relative to the level of reporter product expressed in a second cell containing the steroid intracellular receptor and reporter vector, and contacted with the activator and second compound, as an indication of the potential antagonist activity of the second compound on steroid intracellular receptor-mediated transcription.

15. An assay kit to screen for antagonists of steroid intracellular receptor-mediated transcription comprising a first cell containing asteroid intracellular receptor other than progesterone receptor, progesterone receptor A form, a reporter vector including a gene encoding a reporter product and a promoter which is transcriptionally active in the presence of the steroid intracellular receptor but is a negligible activator of transcription in the presence of the progesterone receptor A form, a second cell containing the steroid intracellular receptor and reporter vector, and an activator of steroid intracellular receptor-mediated transcription, wherein the progesterone receptor A form is a negligible activator of transcription in the first cell, and wherein the contacting of the first cell with the activator and a compound to be assayed yields a level of expressed reporter product that can be compared to the level of expressed reporter product in the second cell when contacted with the activator and second compound, as an indication of the potential antagonist activity of the compound to be assayed on steroid intracellular receptor-mediated transcription.

16. A method for screening progesterone receptor agonist or antagonist for estrogen receptor antagonist activity comprising:

(a) introducing a first vector encoding estrogen receptor and a second vector encoding progesterone receptor A form along with a third reporter vector into a cell in which the progesterone receptor A form is a negligible activator of transcription, wherein the reporter vector includes a gene encoding a reporter product and a promoter which is transcriptionally active in the presence estrogen receptor but is a negligible activator of transcription in the presence of the progesterone receptor A form;

(b) contacting the cell with an estrogen receptor agonist and a progesterone receptor agonist or antagonist; and (c) comparing the level of reporter product expressed in the cell relative to the level of reporter product expressed in a second cell containing estrogen receptor and the reporter vector, and contacted with the estrogen receptor agonist and progesterone receptor agonist or antagonist, as an indication of the potential antagonist activity of the progesterone receptor agonist or antagonist on estrogen receptor-mediated transcription.

17. The method of claim 16, wherein the first and second cells are CV-1 cells.

18. The method of claim 17, wherein the reporter vector comprises a gene encoding luciferase and the ERE-MMTV promoter.

19. The method of claim 16, wherein the estrogen receptor agonist is 17-β-estradiol.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:1:

CCTGTGGGAG CGCTAAGGTC TTC 23